United States Patent
Braham

(10) Patent No.: US 10,493,242 B2
(45) Date of Patent: Dec. 3, 2019

(54) RESPIRATORY AIRWAY AND INTRAVENOUS EXTENSION SYSTEM (RAIVES)

(71) Applicant: Antonio Braham, Sacramento, CA (US)

(72) Inventor: Antonio Braham, Sacramento, CA (US)

( * ) Notice: Subject to any disclaimer, the term of this patent is extended or adjusted under 35 U.S.C. 154(b) by 314 days.

(21) Appl. No.: 15/407,531

(22) Filed: Jan. 17, 2017

(65) Prior Publication Data

US 2018/0200485 A1   Jul. 19, 2018

(51) Int. Cl.
| | |
|---|---|
| *A61M 25/02* | (2006.01) |
| *A61M 5/14* | (2006.01) |
| *A61M 16/00* | (2006.01) |
| *A61M 16/08* | (2006.01) |
| *G16H 40/63* | (2018.01) |
| *G16H 10/60* | (2018.01) |
| *G16H 20/40* | (2018.01) |
| *A61M 39/08* | (2006.01) |

(52) U.S. Cl.
CPC .......... *A61M 25/02* (2013.01); *A61M 5/1413* (2013.01); *A61M 16/0051* (2013.01); *A61M 16/022* (2017.08); *A61M 16/0875* (2013.01); *G16H 10/60* (2018.01); *G16H 20/40* (2018.01); *G16H 40/63* (2018.01); *A61M 2025/024* (2013.01); *A61M 2025/028* (2013.01); *A61M 2039/087* (2013.01); *A61M 2205/18* (2013.01); *A61M 2205/3375* (2013.01); *A61M 2205/3561* (2013.01); *A61M 2205/3592* (2013.01); *A61M 2205/50* (2013.01); *A61M 2205/505* (2013.01); *A61M 2205/8206* (2013.01); *A61M 2209/082* (2013.01)

(58) Field of Classification Search
CPC ............ A61M 25/02; A61M 2025/024; A61M 2025/028; A61M 16/0488; A61M 16/0497; A61M 16/0683; A61M 16/08; A61M 16/0875; A61M 2209/08; A61M 2209/082; A61M 5/1418
See application file for complete search history.

(56) References Cited

U.S. PATENT DOCUMENTS

| | | | | |
|---|---|---|---|---|
| 2007/0142785 A1* | 6/2007 | Lundgaard | .......... | A61M 5/1418 604/179 |
| 2009/0019678 A1* | 1/2009 | Taylor | ................. | A61M 5/1418 24/530 |

OTHER PUBLICATIONS

JannaBand; One Hospital Bed—One Call Button—One JanaBand;; [retrieved on Feb. 5, 2019]; retrieved from the Internet: http://www.janaband.net 1 page.

(Continued)

*Primary Examiner* — Bhisma Mehta
*Assistant Examiner* — James D Ponton
(74) *Attorney, Agent, or Firm* — Fish & Richardson P.C.

(57) ABSTRACT

A respiratory airway and intravenous extension system (RAIVES) apparatus includes a female-configured side plate and a male-configured side plate. A connector spring is configured to engage with and to couple together the female-configured side plate and the male-configured side plate. The connector spring provides an inward spring bias to bias a lower portion of the female-configured side plate and a lower portion of the male-configured side plate together into a default closed position. The RAIVES also includes raised guidance elements and a plurality of securing bands for securing a medical extension device to the raised guidance elements.

12 Claims, 20 Drawing Sheets

(56) References Cited

OTHER PUBLICATIONS

MarketLab; Unique & Hard-to-Find Laboratory and Medical Supplies; "IV Line Holder"; [retrieved on Feb. 5, 2019]; retrieved from the Internet: https://www.marketlab.com/iv-line-holder/p/IVLineHolder/ 1 page.
Da Vinci Medical, Inc.; "IV Line, Medical Tube Holder & Organizer"; [retrieved from the internet on Feb. 5, 2019]; retrieved from the internet: https://www.youtube.com/watch?v=IMofUqH2CTg ; 1 page.
NewMediaWire; "Introducing the Perfect Gift for Nurses on Certified Nurses Day: The Easy View IV Tube Separator!"; [retrieved from the internet on Feb. 5, 2019]; retrieved from the internet: https://app.newmediawire.com/news/531ddac2875a520007b3afd1/introducing-the-perfect-gift-for-nurses-on-certified-nurses-day-the-easy-view-iv-tube-separator ; 4 pages.
The Beata Clasp; [retrieved from the internet on Feb. 5, 2019]; http://www.beataclasp.com/ ; 2 pages.
Research Gate; "Edwards Vamp System"; [retrieved from the internet on Feb. 5, 2019]; retrieved from the internet: https://www.researchgate.net/figure/Edwards-VAMP-system-The-port-to-the-right-of-the-image-is-the-sampling-port-which-is_fig1_236956639 ; 4 pages.
Tucker Hemphill; "IV-Buddy"; [retrieved from the internet on Feb. 5, 2019]; retrieved from the internet: https://www.tuckerhemphill.com/iv-buddy/ ; 19 pages.
Vitality Medical.com; Dale Hold-N-Place Foley Catheter Holder; [retrieved from the internet on Feb. 5, 2019]; retrieved from the internet: https://www.vitalitymedical.com/dale-foley-catheter-holder.html ; 9 pages.

\* cited by examiner

RESPIRATORY AIRWAY AND INTRAVENOUS EXTENSION SYSTEM (RAIVES)

BACKGROUND

Patients in medical facilities are typically attached to various types of monitoring and medically-assistive (for example, intravenous (IV) and respiratory) equipment. Attachment to the medically-assistive equipment is accomplished using various medical extension devices (MEDs) (for example, IV and respiratory tubing, lead wires, cables, and the like). Transferring a patient (for example, from a gurney to a bed or vice versa) or re-positioning the patient (for example, rotating the patient from a supine to a lateral position) while attached to the medically-assistive equipment can be cumbersome due to the attached MEDs.

SUMMARY

The present disclosure describes a respiratory airway and intravenous (IV) extension system (RAIVES).

In an implementation, a RAIVES apparatus includes a female-configured side plate and a male-configured side plate. A connector spring is configured to engage with and to couple together the female-configured side plate and the male-configured side plate. The connector spring provides an inward spring bias to bias a lower portion of the female-configured side plate and a lower portion of the male-configured side plate together into a default closed position. The RAIVES also includes raised guidance elements and a plurality of securing bands for securing a medical extension device to the raised guidance elements.

Some particular implementations include using computer-implemented methods; non-transitory, computer-readable media storing computer-readable instructions to perform the computer-implemented methods; and computer-implemented systems comprising computer memory interoperably coupled with one or more hardware processors configured to perform the computer-implemented methods/the instructions stored on the non-transitory, computer-readable media.

The details of one or more implementations of the subject matter of this specification are set forth in the accompanying drawings and the description below. Other features, aspects, and advantages of the subject matter will become apparent from the description, the drawings, and the claims.

DESCRIPTION OF DRAWINGS

Like reference numbers and designations in the various drawings indicate like elements.

DETAILED DESCRIPTION

Figure 1A:
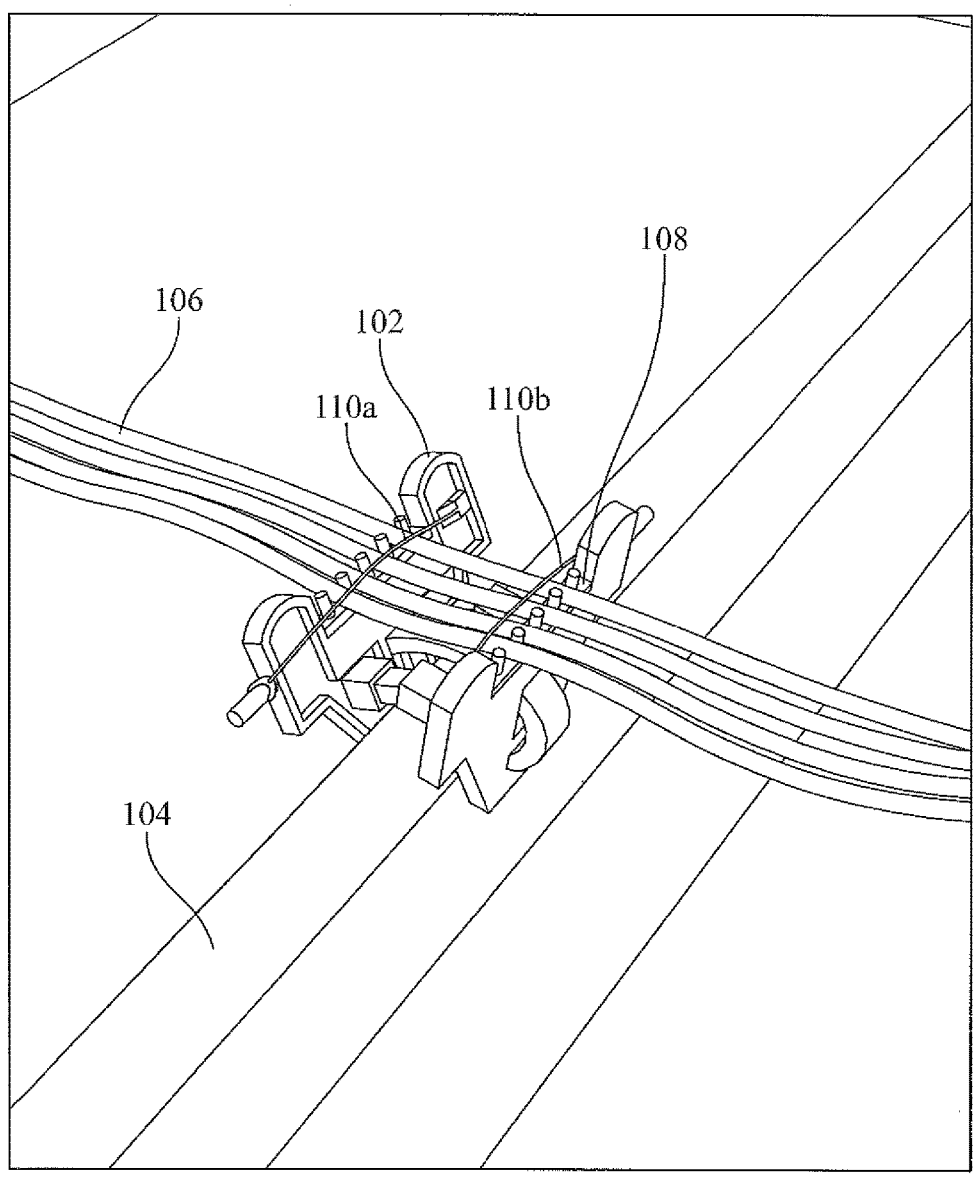
FIG. 1A is a perspective view of an intravenous (IV)-configured respiratory airway IV Extension System (RAIVES), according to an implementation.

The following detailed description describes a respiratory airway and intravenous (IV) extension system (RAIVES) apparatus and use, and is presented to enable any person skilled in the art to make and use the disclosed subject matter in the context of one or more particular implementations. Various modifications, alterations, and permutations of the disclosed implementations can be made and will be readily apparent to those skilled in the art, and the general principles defined herein may be applied to other implementations and applications without departing from scope of the disclosure. Thus, the present disclosure is not intended to be limited to the described or illustrated implementations, but is to be accorded the widest scope consistent with the principles and features disclosed herein.

Patients in medical facilities are typically attached to various types of monitoring and medically-assistive (for example, IV and respiratory) equipment. Attachment to the medically-assistive equipment is accomplished using various medical extension devices (MEDs) (for example, IV and respiratory tubing, lead wires, cables, and the like). Transferring a patient (for example, from a gurney to a bed or vice versa) or re-positioning the patient (for example, rotating the patient from a supine to a lateral position) while attached to the medically-assistive equipment can be cumbersome due to the attached MEDs.

The subject matter described in this disclosure can be implemented in particular implementations so as to realize one or more of the following advantages. First, the described RAIVES permits MEDs (for example, IV and respiratory tubing, lead wires, cables, and the like) to be easily transferred from one patient treatment platform (for example, a gurney or hospital bed) attachment point to another (for example, moved from a gurney rail to a hospital bed rail (or vice versa) or from one hospital bed rail to another hospital bed rail. Second, the RAIVES can keep MEDs organized and grouped for easy identification and maintenance. In some medical facilities (for example, intensive care units (ICUs), emergency rooms (ERs), etc.), it is important that MEDs are kept neatly in proximity to each other and off the medical facility floor where they could be stepped on, tripped over, or contaminated by dirt, organisms, etc. tracked in on footwear. Third, use of the RAIVES MEDs can eliminate medical waste when using medical tape, tongue depressors, and other valuable medical resources to created improvised MED organization solutions. Fourth, the described RAIVES implementations can be configured as a completely disposable medical resource to avoid additional costs (such as, sterilization, etc.) to enable re-use. This can be especially important in situations dealing with hazardous infectious organisms where patient and healthcare provider safety is paramount after medical equipment comes into contact with blood and other bodily fluids. In some implementations, some portions of the RAIVES can be configured of materials that can be sterilized (for example, stainless steel or aluminum) to permit disassembly, cleaning, sterilization in an autoclave/disinfecting chemical, and reassembly. In the general use scenario, portions such as the guide plate and securing bands (see below for more detail) can be replaceable with new, sterile components configured as desired. Fifth, in some implementations, the RAIVES can be configured of recyclable, biodegradable, or environmentally-friendly materials to protect the environment. Other advantages will be apparent to those of ordinary skill in the art.

At a high-level, the RAIVES is "clip"-type apparatus mountable on medical equipment, particularly rails of patient treatment platforms, such as gurneys and hospital beds. The RAIVES permits MEDs to be organized and managed between a medical-assistive device and a patient on a patient treatment platform. The RAIVES allows MEDs attached to a patient to be easily moved from one treatment platform to another treatment platform (for example, when moving a patient to/from an ICU or ER, to a different hospital room, from an ambulance gurney to an ICU or ER, and the like).

Turning now to FIG. 1A, FIG. 1A is a perspective view 100a of an intravenous (IV)-configured respiratory airway IV Extension System (RAIVES), according to an implementation. As illustrated, the RAIVES 102 is attached to an example hospital bed rail 104. MEDs 106 (here illustrated as a group of various IV tubes, lead wires, and cables) are disposed across/between a row of raised guidance elements 108 (here, illustrated in a cylindrical/"bristle"-type shape) attached to the upper portion of the RAIVES 102 to guide the MEDs 106 across the upper portion of the RAIVES 102. Securing bands 110a and 110b are used to secure the MEDs 106 between the raised guidance elements 108 to permit secure organization and movement of the MEDs 106 if desired to a different location on the hospital bed rail 104 (including a different hospital bed rail on the same hospital bed) or to a different patient treatment platform as described above.

Figure 1B:
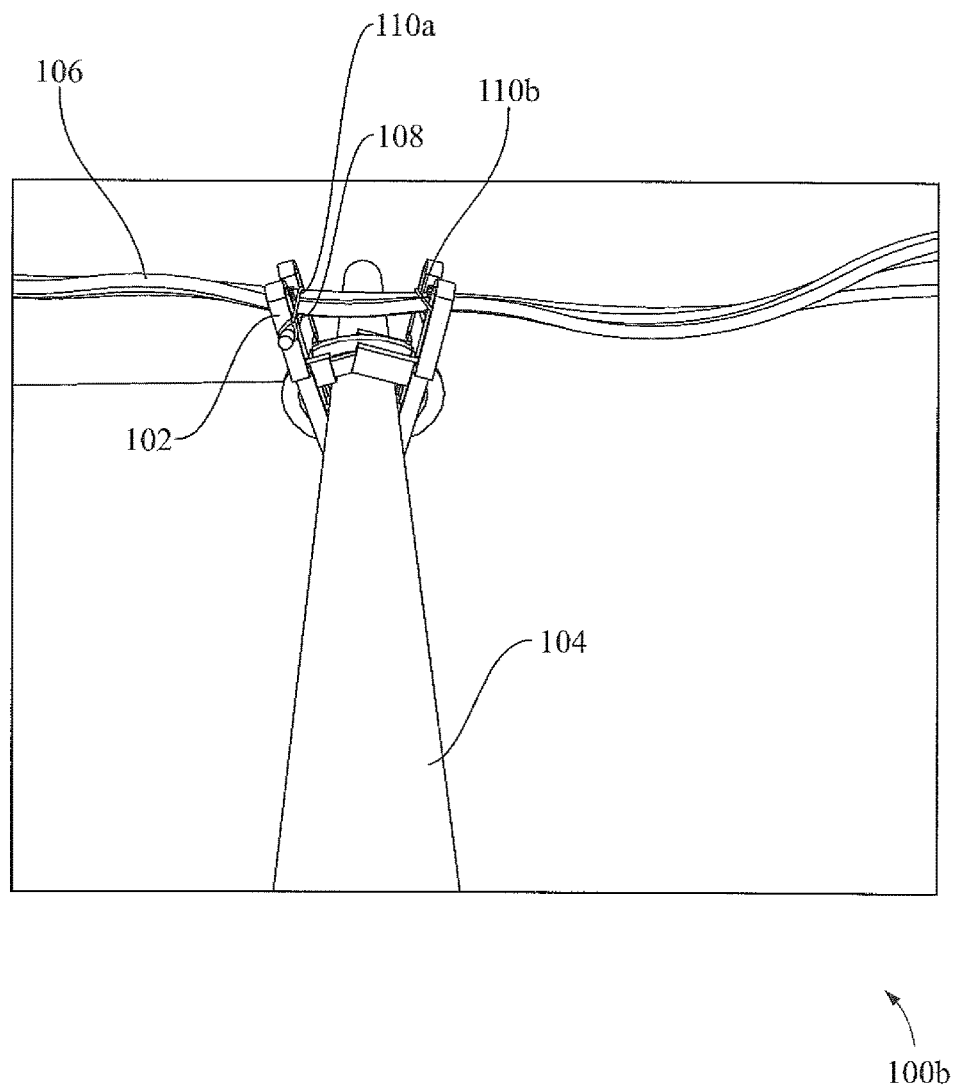
FIG. 1B is an alternative perspective view of the RAIVES of FIG. 1A, according to an implementation.

FIG. 1B is an alternative perspective view 100b of the RAIVES of FIG. 1A, according to an implementation. The alternative perspective view of the RAIVES 102 is from an end and illustrates how the RAIVES 102 is configured to clip securely to the circumference of the example hospital bed rail 104. Some implementations of the RAIVES 102 can be configured in varying sizes to permit secure attachment to differing sizes of patient treatment platform rails or other structures (for example, an IV bag stand, lamp stand, or other vertical standing tubular structure). In some implementations, the RAIVES 102 can be directly clipped to patient treatment platform linens, patient clothing, and the like.

Figure 2:
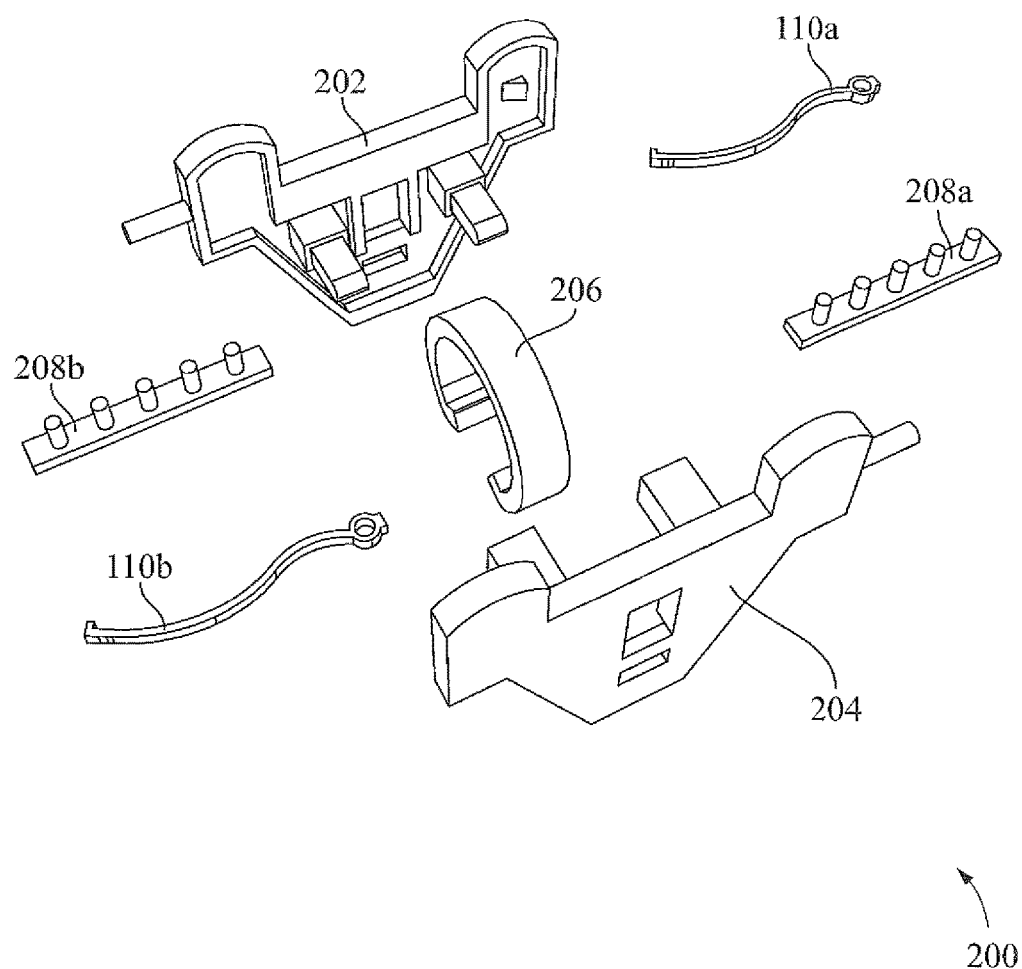
FIG. 2 is an exploded view of the RAIVES of FIGS. 1A and 1B, according to an implementation.

FIG. 2 is an exploded view 200 of the RAIVES of FIGS. 1A and 1B, according to an implementation. As illustrated, the RAIVES includes a female-configured side plate 202, male-configured side plate 204, connector spring 206, raised guidance elements 208a/208b (for example, raised guidance elements 108 of FIGS. 1A and 1B), and securing bands 110a/110b.

Each of the upper portions of the female-configured side plate 202 and male-configured side plate 204 are configured with two pinch tabs (for example, refer to elements 302a and 302b in FIGS. 3A and 4A, respectively) to permit the upper surfaces of female-configured side plate 202 and the male-configured side plate 204 to be pinched together. Each of the female-configured side plate 202 and the male-configured side plate 204 is also configured to define a connector spring engagement slot and a connector spring locking slot (for example, refer to elements 312 and 314, respectively in FIGS. 3A and 4A, respectively). In typical implementations, the female-configured side plate 202, male-configured side plate 204, and connector spring 206 are configured of plastic, rubber, silicon, or other disposable material. The connector spring 206 is configured of a material of sufficient plasticity (for example, various plastics, composites, etc. and including the same material used for the female-configured side plate 202 and the male-configured side plate 204) to provide an inward spring bias to preserve the shape of the connector spring 206 but allowing the connector spring to be opened and closed without fracture or fatigue of the material. In some implementations, one or more elements of the IV-configured RAIVES (for example, the female-configured side plate 202 and the male-configured side plate 204 and the connector spring 206) can be configured of a material (for example, plastics, metals or ceramics) that can be disassembled, cleaned, sterilized in an autoclave or by chemical exposure (without sustaining damage due to high temperatures or chemical exposure, respectively), and reassembled for re-use.

Figure 7:
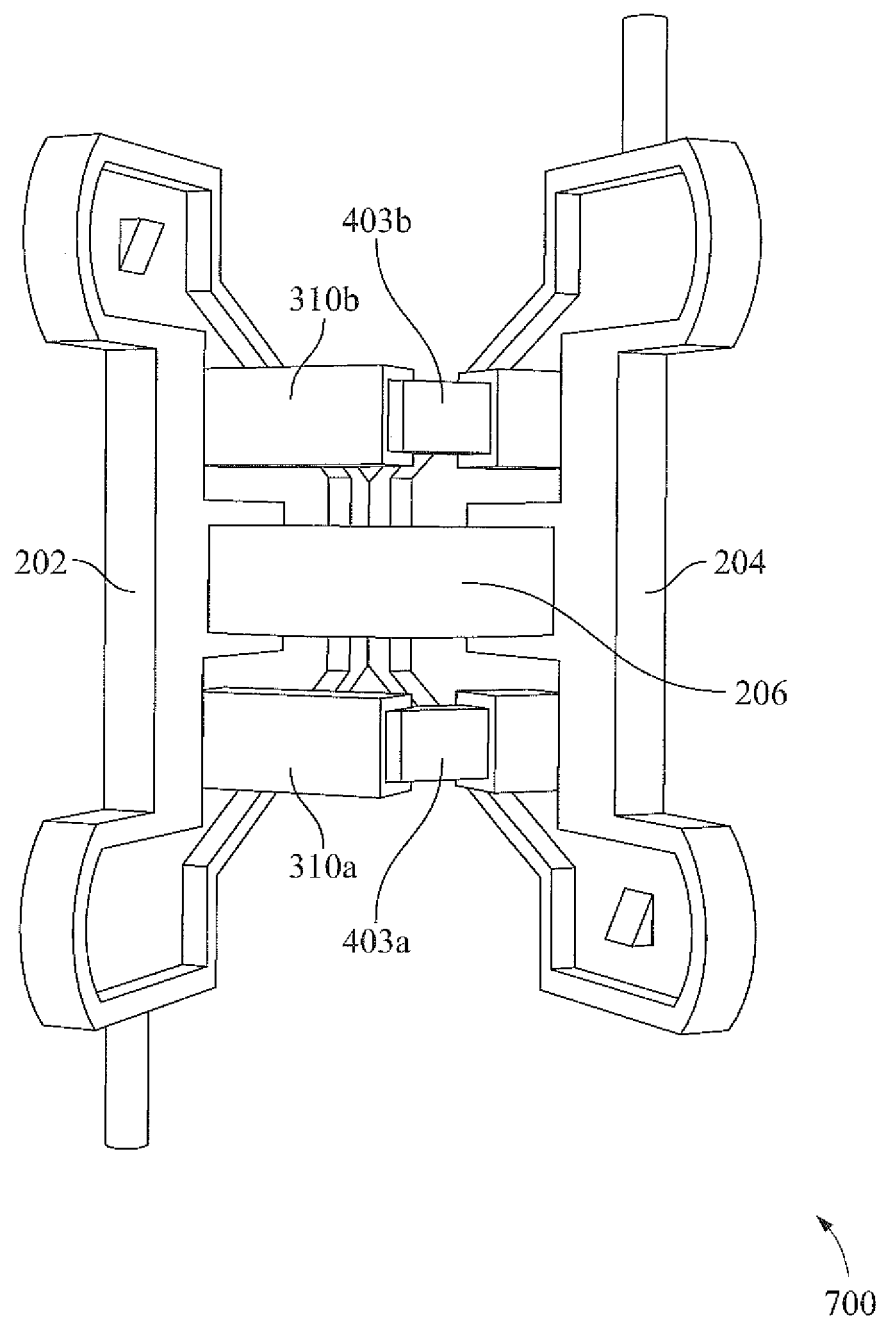
FIG. 7 is a top view of the major structural components of the RAIVES of FIG. 1A, according to an implementation.
Figure 8:
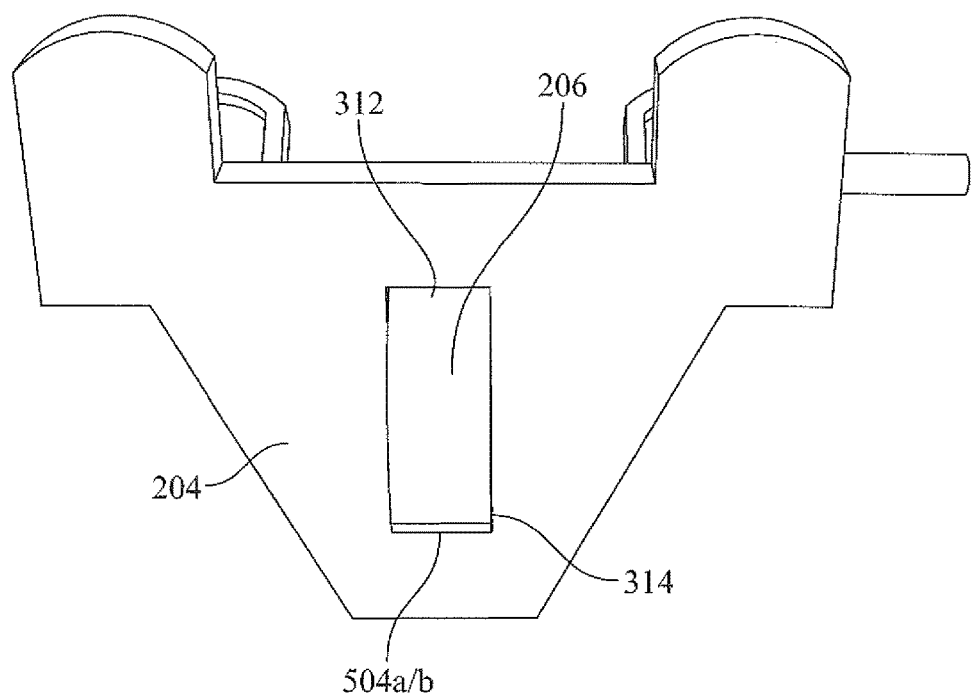
FIG. 8 is a side view of the major structural components of the RAIVES of FIG. 1A, according to an implementation.

Each angled locking end of the connector spring 206 (for example, refer to elements 502a and 502b in FIG. 5) is configured to pass through the connector spring engagement slot from the interior of the female-configured side plate 202 and the male-configured side plate 204 and to engage from the exterior of the female-configured side plate 202 and the male-configured side plate 204 with the connector spring locking slot defined in each of the female-configured side plate 202 and the male-configured side plate 204 (for example, refer to FIG. 8). An inward spring bias of the connector spring 206 inwardly biases the female-configured side plate 202 and the male-configured side plate 204 together to couple female and male hinge elements (for example, refer to elements 310a/310b and 402a/402b of FIGS. 3A and 4A, respectively) configured as part of the female-configured side plate 202 and the male-configured side plate 204, respectively (for example, refer FIGS. 7, 9, and 11). The inward spring bias of the connector spring 206 biases the female-configured side plate 202 and the male-configured side plate 204 into a default closed configuration at the lower portions of the female-configured side plate 202 and the male-configured side plate 204 (for example, refer to FIG. 10). This inward spring bias provides mechanical force necessary to "clip" the RAIVES to patient treatment platforms or other structures as described above.

With respect to the female-configured side plate 202 (and, analogously, the male-configured side plate 204 and securing band 110b), a securing band 110a is attached to one side of the female-configured side plate 202. The securing band 110a is typically stretched to engage with a locking pin configured on the opposite side of the female-configured side plate 202 (for example, refer to FIGS. 1A, 1B, and 3A (element 306)). The elastic tension generated by the stretched and secured securing band 110a is used to secure MEDs to the raised guidance elements 208a/208b (refer to FIGS. 3A and 6C for additional details).

In an alternative use (not illustrated), the securing band 110a could be stretched to engage with the locking pin configured as part of the male-configured side plate 204 (and, analogously, the securing band 110b could be stretched to engage with the locking pin configured as part of the female-configured side plate 202). This would create an "X"-type configuration to secure MEDs running between raised guidance elements 208a/208b.

In another alternative configuration (not illustrated), locking pins (or securing band attachment points proximate to where locking pins would be configured) can be configured on both sides of each of the female-configured side plate 202 and the male-configured side plate 204. Each end of a securing band can be attached to a locking pin on the same end of the female-configured side plate 202 and the male-configured side plate 204. Each securing band can be configured to be stretched and to attach together in the middle of each securing band to form a similar "X"-type configuration as described above. In this configuration, the attachment mechanism could be similar to hooks, button/loop, toggle button/loop, etc. To prevent the securing bands from being lost from the attachment points, each end of the securing band can be configured to attach to a locking pin (or to the above-mentioned securing band attachment point) using, for example, screws, clamps, hooks, male/female interlocking structures, etc.

In another alternative configuration (not illustrated), locking pins can be configured on the same side of each of the female-configured side plate 202 and the male-configured side plate 204. However, the locking pins are configured on the interior of the associated side pinch tab and project inward toward each other. On the other side of each of the female-configured side plate 202 and the male-configured side plate 204, both securing band attachment points are configured to couple with securing bands. At the non-attached end of each securing band, a common dual-hook assembly is attached. The dual-hook assembly can be pulled from one side of the RAIVES to hook over each of the inwardly-projecting locking pins. In this manner, a single stretching motion is required to secure MEDS running between raised guidance elements 208a/208b. In some implementations, the dual-hook assembly, can be configured with a tab or other structure for each gripping with finger tips.

Figure 6A:
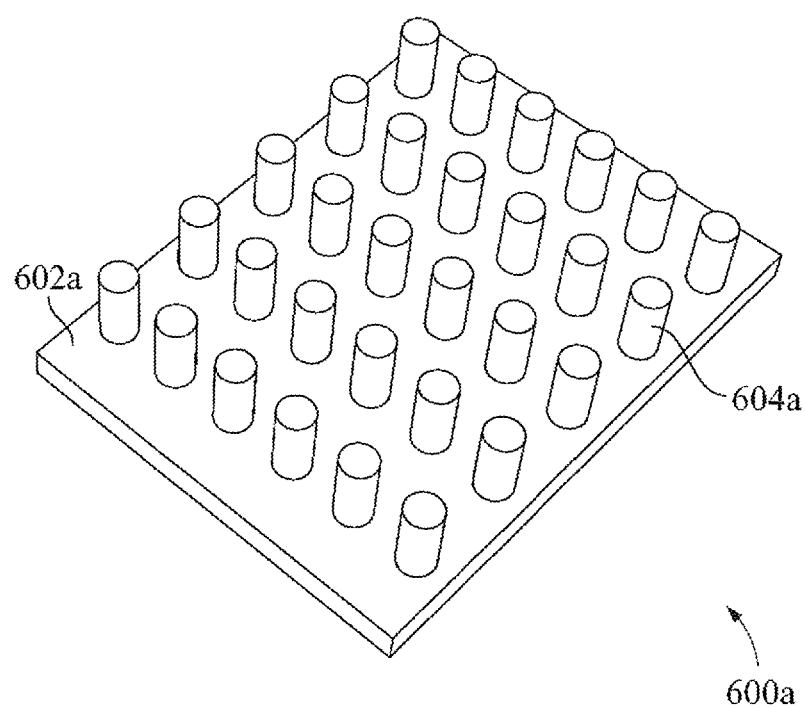
FIG. 6A is a perspective view of an IV-type guide plate, according to an implementation.

Raised guidance elements 208a/208b are typically configured in rows and attached (for example, using an adhesive, screws, clamps, male/female interlocking elements, fused using heat to melt materials together, etc.) to an attachment surface configured into the female-configured side plate 202 and the male-configured side plate 204 between the two pinch tabs configured into each of the female-configured side plate 202 and the male-configured side plate 204, respectively, and to guide/semi-secure MEDS (for example, IV tubes) along its surface (refer to FIG. 6A for additional detail). The raised guidance elements 208a/208b are typically configured of an elastomeric material (for example, rubber, silicon, or plastic) that can compress, stretch, and bend. In typical implementations, the raised guidance elements 208a/208b are integrally molded to a sheet of elastomeric material) and permanently attached to the above-mentioned attachment surface of each of the female-configured side plate 202 and the male-configured side plate 204. In alternative implementations, the raised guidance elements 208a/208b securing mechanism can be configured (for example, with a less-than permanent adhesive) to permit removal of a particularly configured raised guidance element 208a/208b (for example, for use with a particularly-sized IV tubing) and replacement with a differently configured raised guidance elements 208a/208b (for example, for use with smaller or larger diameter IV tubing).

Alternative implementations of the described RAIVES (including the configuration described in FIGS. 13A-13B) can be configured to support multiple connector springs. For example, the female-configured side plate 202 and the male-configured side plate 204 can be configured to be wider (here, allowing more MEDS to be guided/organized), the space between the pinch tabs can be increased to permit the use of a wider series of raised guidance elements 208a/208b, each of the female-configured side plate 202 and the male-configured side plate 204 can be configured to define more than one connector spring engagement slot and connector spring locking slot, and additional female and male hinge elements can be configured on each of the female-configured side plate 202 and the male-configured side plate 204, respectively, to support additional mechanical force. These described alterations should be readily apparent to those of ordinary skill in the art.

The following description provides an example use case of the RAIVES configuration illustrated in at least FIGS. 1A-1B and 2. In some implementations, various described steps of the use case can, consistent with this disclosure, be performed in a different order. To open and engage the RAIVES with a structure (for example, a hospital bed rail), the RAIVES can be held in the hands by a human user and the pinch tabs on each of the female-configured side plate 202 and the male-configured side plate 204 pressed together. As a particular example, a thumb from each hand can be placed on the pinch tabs of one side plate, an index finger from the corresponding hand can be placed on the opposite/corresponding pinch tab of the other side plate, and the thumb and index fingers brought together on each hand. Pressing the female-configured side plate 202 and the male-configured side plate 204 together will produce force to overcome the inward spring bias of the connector spring 206, cause the female and male hinge elements configured as part of the female-configured side plate 202 and the male-configured side plate 204 to bear against each other and rotate against an engagement portion configured as part of the male hinge element, and result in the lower portions of the female-configured side plate 202 and the male-configured side plate 204 to open for engagement with a desired structure (for example, refer to FIG. 11). Once secured to a desired structure, MEDS can be run between the raised guidance elements 208*a*/208*b* perpendicular to the rotational axis of opening the RAIVES. Once the MEDS are in place, the securing bands 110*a*/110*b* attached to each of the female-configured side plate 202 and the male-configured side plate 204, respectively, are stretched over the MEDS and engaged with the locking pin configured into each of the female-configured side plate 202 and the male-configured side plate 204 to secure the MEDS between the raised guidance elements 208*a*/208*b*.

Figure 3A:
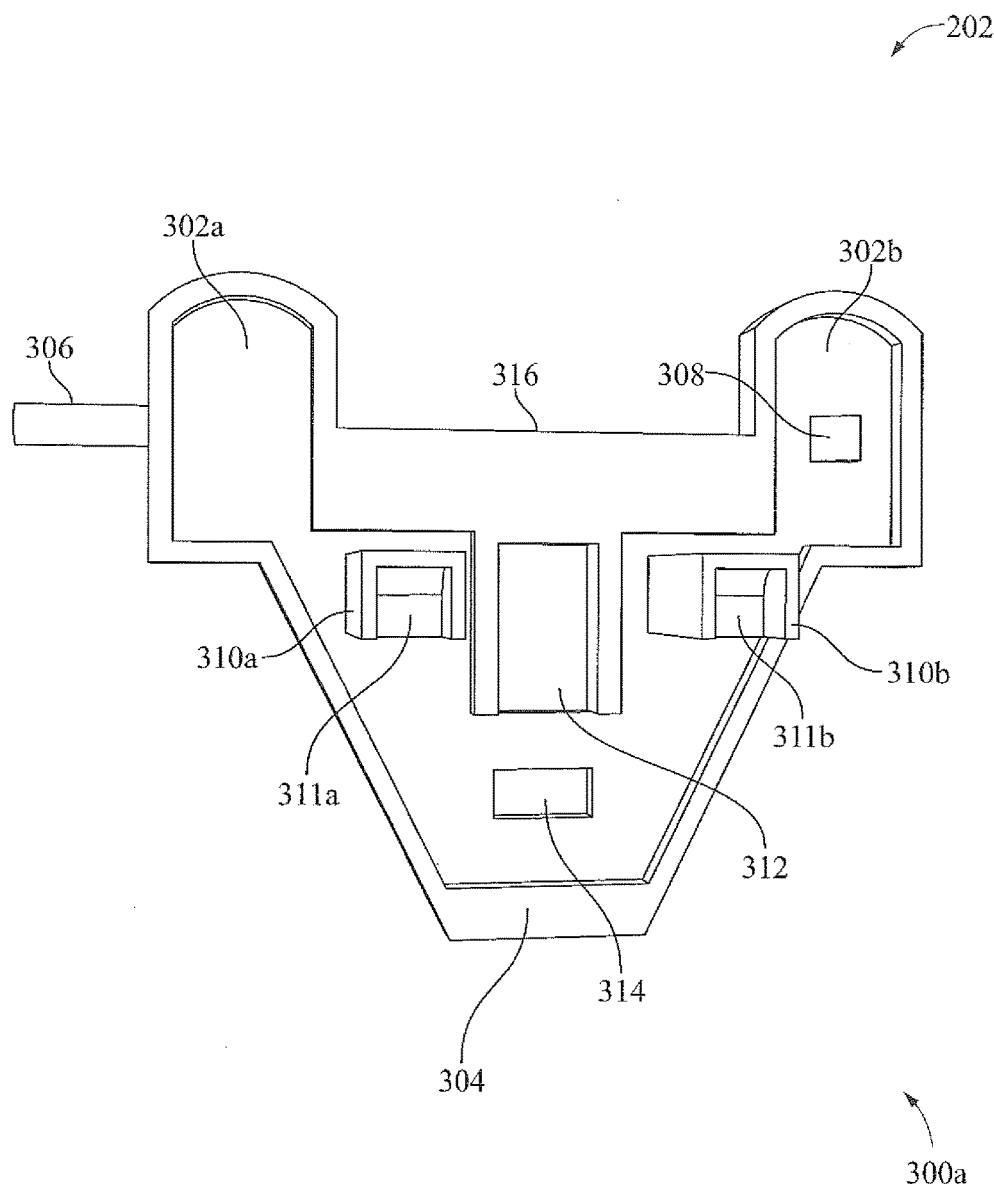
FIG. 3A is an inside view of a female-configured side plate (the female-configured side plate of FIG. 2), according to an implementation.

FIG. 3A is an inside view 300*a* of a female-configured side plate (the female-configured side plate 202 of FIG. 2), according to an implementation. The illustrated female-configured side plate 202 includes pinch tabs 302*a*/302*b*, gripping surface 304, locking pin 306, securing band attachment point 308, female hinge elements 310*a*/310*b* and corresponding engagement pockets 311*a*/311*b*, connector spring engagement slot 312, connector spring locking slot 314, and attachment surface 316.

As stated above, the pinch tabs 302*a*/302*b* provide engagement surfaces for fingers of healthcare professionals to permit the upper surfaces of female-configured side plate 202 and the male-configured side plate 204 to be pinched together. The locking pin 306 is configured proximate to, and to the side of, pinch tab 302*a*. A securing band attachment point 308 is configured on the inner surface of the pinch tab 302*b*.

Gripping surface 304 is used to clip the RAIVES to a desired structure. Although not illustrated, gripping surface 304 can be further configured with an elastomeric-type surface (for example, an additionally adhered rubber, silicon, or similar type of material) or integrally configured with a spiked/dimpled surface to increase clamping efficiency to the desired structure.

In typical implementations, a stationary end of the securing band 110*a* (for example, refer to element 602*c* of FIG. 6C) is attached to the securing band attachment point 308 (for example, using adhesive, a hook/loop, screws, clips, or male/female interlocking structures). For example, the stationary end of the securing band 110*a* can be a loop and attached to a securing band attachment point 308 configured as a hook or screw head (or vice versa). In another implementation, the stationary end of the securing band 110*a* can be attached to the securing band attachment point 308 using a strong adhesive (such as a cyanoacrylate, epoxy, etc.).

In typical implementations, an engagement end of the securing band 110*a* can be configured with an engagement ring (for example, refer to element 604*c* of FIG. 6C) that is configured to engage with (for example, slip over) the locking pin 306 when the securing band 110*a* is stretched the length of the female-configured side plate 202. The elastic tension generated by the stretched and secured securing band 110*a* is used to secure MEDs between the raised guidance elements 208*a*/208*b*.

As previously mentioned, the female-configured side plate 202 is also configured to define the connector spring engagement slot 312 and the connector spring locking slot 314. An angled locking end (for example, refer to either element 502*a* or 502*b* in FIG. 5) of the connector spring 206 is configured to pass through the connector spring engagement slot 312 from the interior of the female-configured side plate 202 and to engage with the connector spring locking slot 314 from the exterior of the female-configured side plate 202 to couple the female-configured side plate 202 and the male-configured side plate 204 together.

The attachment surface 316 configured into the female-configured side plate 202 is used to attach, if installed, raised guidance elements (for example, raised guidance elements 208*a*/208*b*). As described above, raised guidance elements 208*a*/208*b* are typically configured to be permanently secured using an adhesive, screws, clamps, male/female interlocking elements, etc. In alternative implementations, the raised guidance elements 208*a*/208*b* can be secured with a less-than permanent method (for example, a removable adhesive, etc.) to permit removal of particularly configured raised guidance elements 208*a*/208*b* (for example, for use with a particularly-sized IV tubing) and replacement of the particularly configured raised guidance elements 208*a*/208*b* with differently configured raised guidance elements 208*a*/208*b* (for example, for use with smaller or larger diameter IV tubing).

In one implementation, the female-configured side plate 202 (and, analogously, the male-configured side plate 204) measures approximately 10.5 cm in width at the widest point, 9.5 cm high at the highest point, and 0.5 cm thick. In particular, the female hinge elements 310*a*/310*b* each measure approximately 2.4 cm in height, 1.2 cm in width, and 0.8 cm in length. The engagement pockets 311*a*/311*b* measure approximately 0.9 cm in width, 0.6 cm in length, and 1.0 cm in engagement depth (for a corresponding engagement portion of the male hinge element—for example, refer to elements 403*a*/403*b* of FIG. 4A).

Although not illustrated, in some implementations, each engagement pocket 311*a*/311*b* can be configured with an elastomeric-type buffer material (for example, rubber, silicon, plastic, etc.) to cushion the engagement of the female hinge elements 310*a*/310*b* and the corresponding engagement portions of the male hinge elements. In an alternative implementation, each engagement portions of the male hinge elements can be configured with an elastomeric-type buffer material (for example, a cap that covers some or all of the engagement portions of the male hinge elements).

Figure 3B:
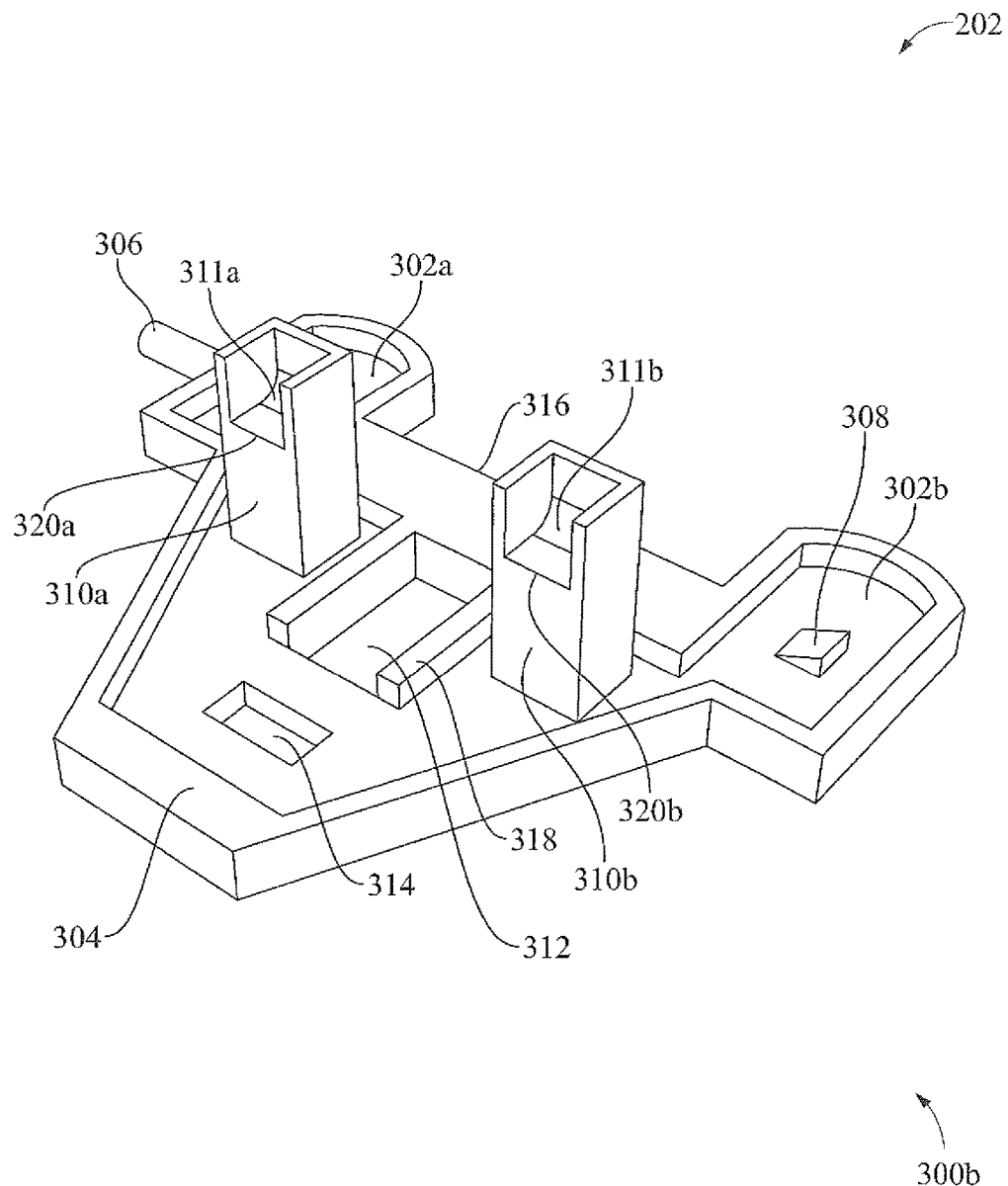
FIG. 3B is a perspective view of the female-configured side plate of FIG. 3A, according to an implementation.

FIG. 3B is a perspective view 300*b* of the female-configured side plate of FIG. 3A, according to an implementation. FIG. 3B illustrates that the female-configured side plate 202 can be configured with a reinforcement ridge 318 partially surrounding the connector spring engagement slot 312 and engagement lips 320*a*/320*b* configured as part of the engagement pockets 311*a*/311*b*. The engagement lips 320*a*/320*b* help prevent the engagement portion of the male hinge elements from sliding out of the engagement pockets 311*a*/311*b* when the female-configured side plate 202 and the male-configured side plate 204 are pressed together.

Figure 3C:
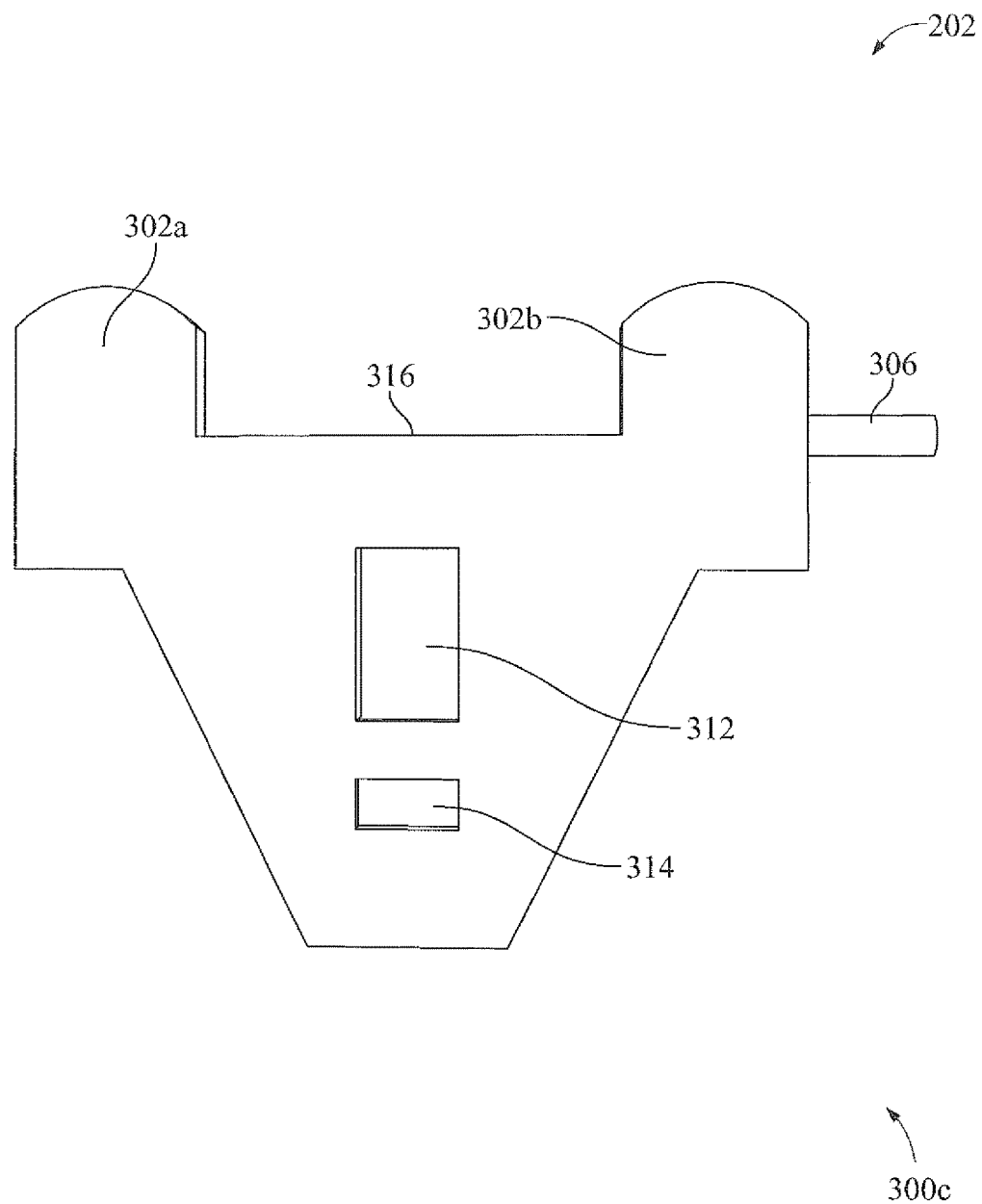
FIG. 3C is an exterior view of the female-configured side plate of FIG. 3A, according to an implementation.

FIG. 3C is an exterior view 300*c* of the female-configured side plate of FIG. 3A, according to an implementation. FIG. 3C illustrates the exterior engagement surfaces of the pinch tabs 302*a*/302*b* of the female-configured side plate of FIG. 3A. Although not illustrated, in some implementations, the exterior engagement surfaces (for example, where finger tips would be placed) of the pinch tabs 302*a*/302*b* can be further configured with an elastomeric-type surface (for example, an additionally adhered rubber, silicon, or similar type of material) or integrally configured with a spiked/dimpled surface to increase friction/surface roughness of the engagement surfaces.

Figure 4A:
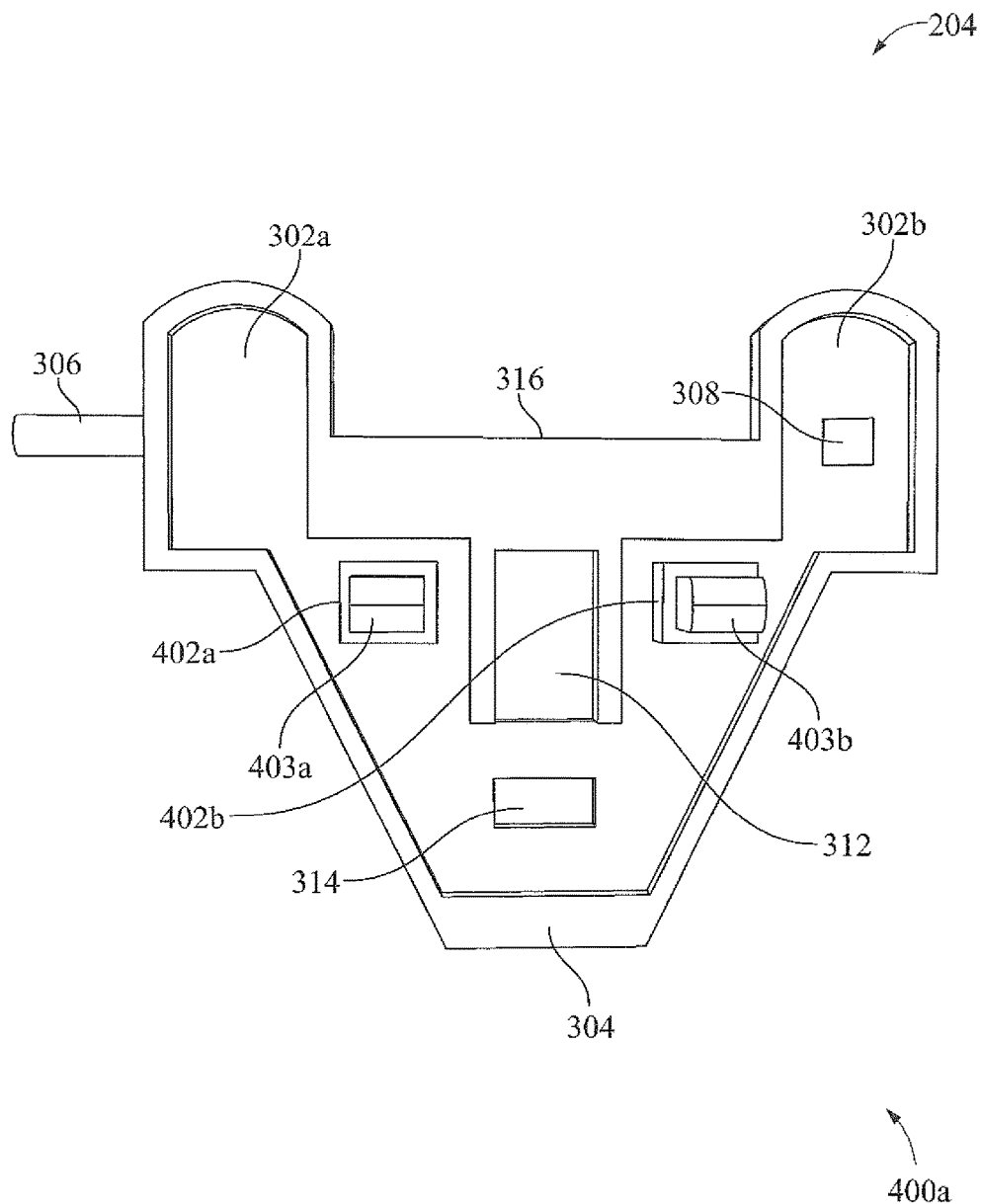
FIG. 4A is an inside view of a male-configured side plate (the male-configured side plate of FIG. 2), according to an implementation.

FIG. 4A is an inside view 400*a* of a male-configured side plate (the male-configured side plate 204 of FIG. 2), according to an implementation. The description of FIG. 3A is applicable to the interior configuration of the male-configured side plate 204 with the exception of the male hinge elements 402a/402b and the corresponding engagement portions 403a/403b of the male hinge elements 402a/402b. FIG. 4A illustrates that, of the engagement portions 403a/403b, each engagement surface is semi-cylindrical. The corresponding inner surface of the above-described engagement pockets 311a/311b are configured to engage with the engagement surface of the engagement portions 403a/403b. In other implementations, the engagement surface shape of the engagement portions 403a/403b and the inner surface shape of the engagement pockets 311a/311b can be configured differently.

Figure 4B:
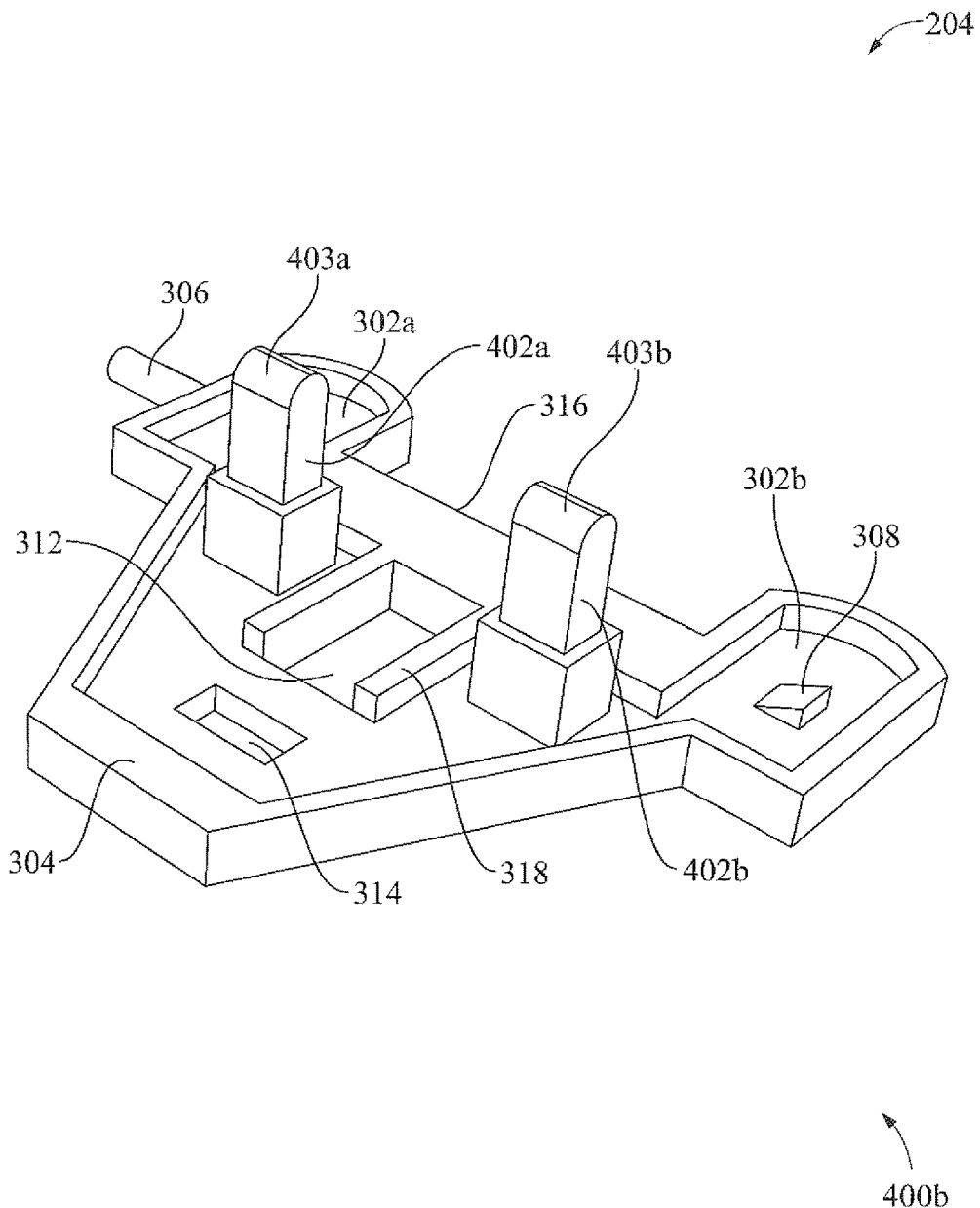
FIG. 4B is a perspective view of the male-configured side plate of FIG. 4A, according to an implementation.

FIG. 4B is a perspective view 400b of the male-configured side plate of FIG. 4A, according to an implementation. The description of FIG. 3A is also applicable to the interior configuration of the male-configured side plate 204 with the exception of the male hinge elements 402a/402b and the corresponding engagement portions 403a/403b of the male hinge elements 402a/402b. Note that the exterior view of the male-configured side plate of FIGS. 4A and 4B is identical to that of FIG. 3C.

Figure 5:
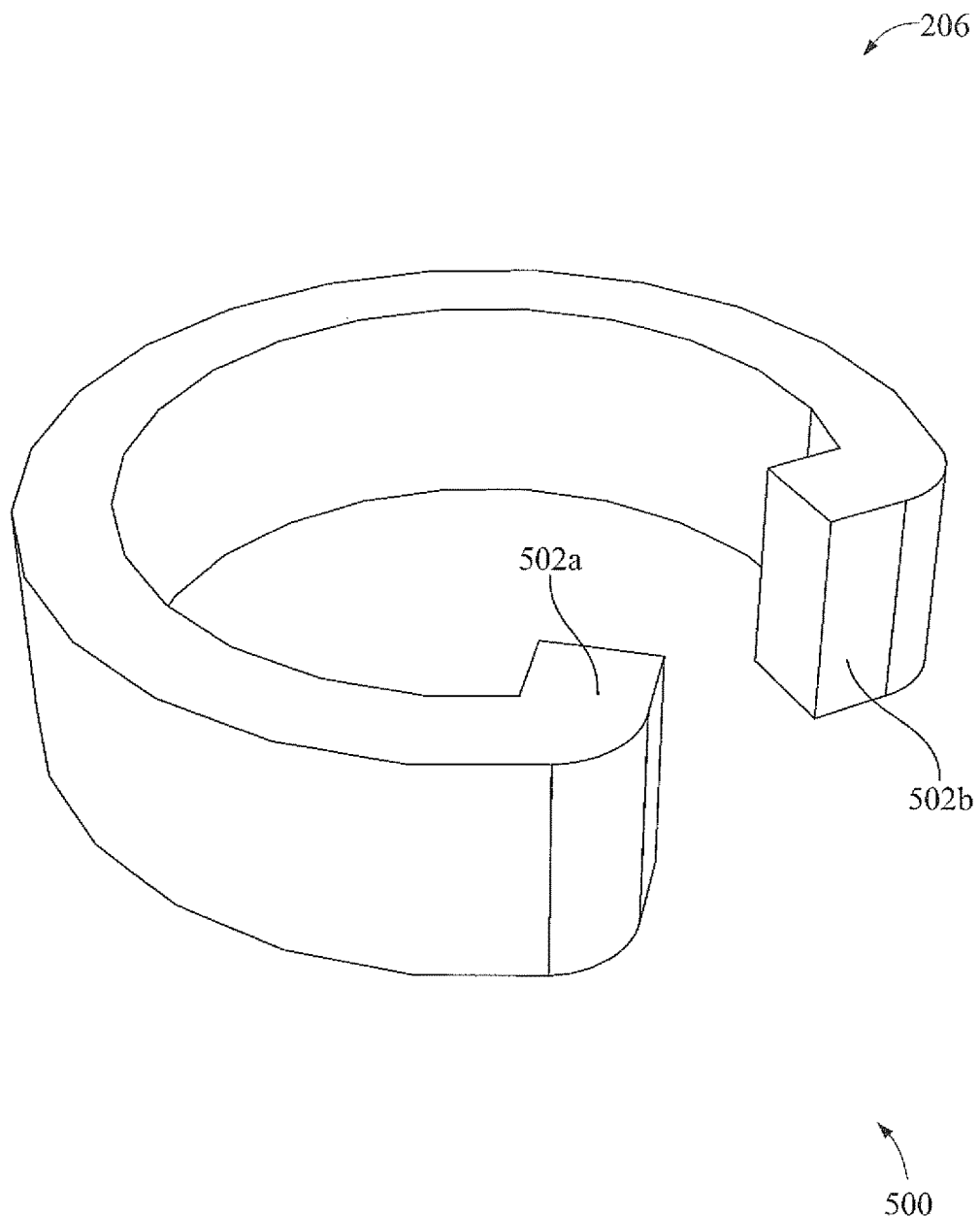
FIG. 5 is a perspective view of a connector spring (the connector spring of FIG. 2), according to an implementation.

FIG. 5 is a perspective view 500 of a connector spring (the connector spring 206 of FIG. 2), according to an implementation. Angled locking ends 502a/502b of the connector spring 206 are configured to pass through the connector spring engagement slot 312 from the interior of the female-configured side plate 202 and male-configured side plate 204 and to engage with the connector spring locking slot 314 from the exterior of the female-configured side plate 202 and male-configured side plate 204 to couple the female-configured side plate 202 and male-configured side plate 204 together. Each angled locking end 502a/502b provides a locking engagement with a corresponding connector spring locking slot 314 in each of the female-configured side plate 202 and male-configured side plate 204.

In one implementation, the connector spring 206 measures approximately 1.0 cm in depth, 5.0 cm in width at the outside diameter at the widest point/4.3 cm in width at the inside diameter at the widest point, and 5.3 cm in height at the highest point. In this implementation, the angled locking ends 502a/502b measure approximately 2.0 cm apart at their closest point and 2.5 cm at their farthest point.

In typical implementations, the inside diameter of the connector spring 206 can be selected to wrap around a desired structure to mount the RAIVES to. For example, the inside diameter of the connector spring 206 can be selected to approximately match the outside diameter of a hospital bed rail where the RAIVES will be attached.

FIG. 6A is a perspective view 600a of an IV-type guide plate, according to an implementation. In some implementations, guide plate 602a can be configured with a series of raised guidance elements 604a (similar to that illustrated in FIGS. 1A and 2). When arranged in a grid-like pattern as illustrated in FIG. 6A, MEDS can be positioned against the surface of the guide plate 602a and between the raised guidance elements 604a. The raised guidance elements 604a are configured to prevent sideways movement of MEDS when secured with securing bands 110a/110b. In other implementations, the raised guidance elements 604a can be configured at each end of the guide plate 602a (for example, one or two rows) while the rest of the guide plate is devoid of additional raised guidance elements 604a.

Guide plate 602a is configured to be attached (for example, using an adhesive, screws, clamps, male/female interlocking elements, fused using heat to melt materials together, etc.) to an attachment surface configured into the female-configured side plate 202 and the male-configured side plate 204 between the two pinch tabs (for example, pinch tabs 302a and 302b of FIGS. 3A, 3B, and 3C) configured into each of the female-configured side plate 202 and the male-configured side plate 204, respectively, and to guide/semi-secure MEDs (for example, IV tubes) along its surface between the raised guidance elements 604a. Guide plate 602a is typically configured of an elastomeric/foldable material (for example, rubber, silicon, plastic, or cloth) that can compress and stretch when the female-configured side plate 202 and the male-configured side plate 204 are pushed together. Guide plate 602a can be configured of varying thickness depending upon a particular configuration material and so as to not impede simple opening and closing operations of the RAIVES. In typical implementations, the guide plate 602a is permanently attached to an attachment surface of each of the female-configured side plate 202 and the male-configured side plate 204. In alternative implementations, the guide plate 602a securing mechanism can be configured (for example, with a less-than permanent adhesive) to permit removal of a particularly configured guide plate 602a (for example, for use with a particularly-sized IV tubing) and replacement with a differently configured guide plate 602a (for example, for use with smaller or larger diameter IV tubing).

In some implementations, the size (width and height), spacing, and number of the raised guidance elements 604a can be varied to support different MED sizes (for example, different diameter IV tubing). In some implementations, one or more raised guidance elements 604a can be configured to contain a sensor element configured to be analyzed by a computer (see below for additional detail).

In some implementations, the guide plate 602a can be used simply as a cover for the connector spring 206 and other elements of the RAIVES. In these implementations, the guide plate 602a is not configured to provide guidance/organization of MEDS.

In one implementation, the guide plate 602a measures approximately 7.0 cm in length, 5.0 cm in width, and less than 0.1 mm in thickness. As described above, thickness of the guide plate 602a can particularly vary based on configuration material, etc.

Figure 6B:
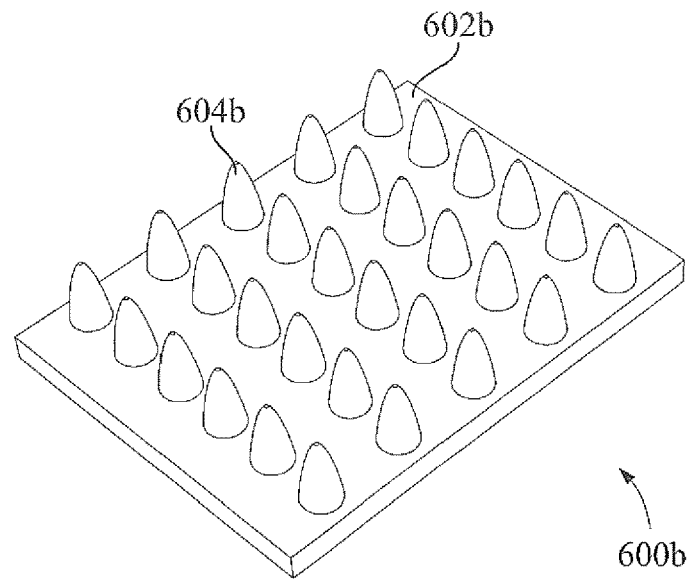
FIG. 6B is a perspective view of an alternatively-configured IV-type guide plate, according to an implementation.

FIG. 6B is a perspective view 600b of an alternatively-configured IV-type guide plate, according to an implementation. FIG. 6B illustrates the alternatively-configured guide plate 602b with conical-type raised guidance elements 604b (for example, shaped similar to a cone, blunted/truncated cone, bi-conic, or other shape). In other implementations, the alternatively-configured raised guidance elements 604b can be configured at each end of the guide plate 602b (for example, one or two rows) while the rest of the guide plate is devoid of additional raised guidance elements 604b. As in FIG. 6A, the size (width and height), spacing, and number of the alternatively-configured raised guidance elements 604b can be varied to support different MED sizes (for example, different diameter IV tubing). In some implementations, one or more alternatively-configured raised guidance elements 604b can be configured to contain a sensor element configured to be analyzed by a computer (see below for additional details).

Figure 6C:
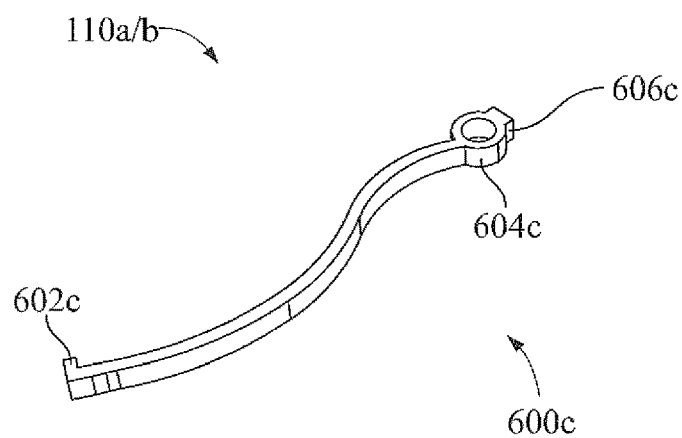
FIG. 6C is a perspective view of securing band (a securing band of FIG. 2), according to an implementation.

FIG. 6C is a perspective view 600c of a securing band (the securing band 110a/110b of FIG. 2), according to an implementation. Securing band 110a/110b includes a stationary end 602c and engagement ring 604c as describe above. Additionally, in some implementations, a grasping tab 606c can be configured as part of the engagement ring 604c. The grasping tab 606c can be used by securely grasping the engagement ring 604c end of the securing band 110a/110b to permit stretching and engagement of the securing band 110a/110b with a locking pin 306.

FIG. 7 is a top view 700 of the major structural components of the RAIVES of FIG. 1A, according to an implementation. FIG. 7 illustrates the above-described inward spring bias of the connector spring 206 inwardly biasing the female-configured side plate 202 and the male-configured side plate 204 together to couple the female and male hinge elements (310a/310b and 403a/403b, respectively) configured as part of the female-configured side plate 202 and the male-configured side plate 204, respectively. The inward spring bias of the connector spring 206 biases the female-configured side plate 202 and the male-configured side plate 204 into a default closed configuration at the lower portions of the female-configured side plate 202 and the male-configured side plate 204.

FIG. 8 is a side view 800 of the major structural components of the RAIVES of FIG. 1A, according to an implementation. FIG. 8 illustrates angled locking ends 502a/502b of the connector spring 206 passing through the connector spring engagement slot 312 from the interior of a female- or male-configured side plate 202/204 and engaging with the connector spring locking slot 314 from the exterior of the female- or male-configured side plate 202/204.

Figure 9:
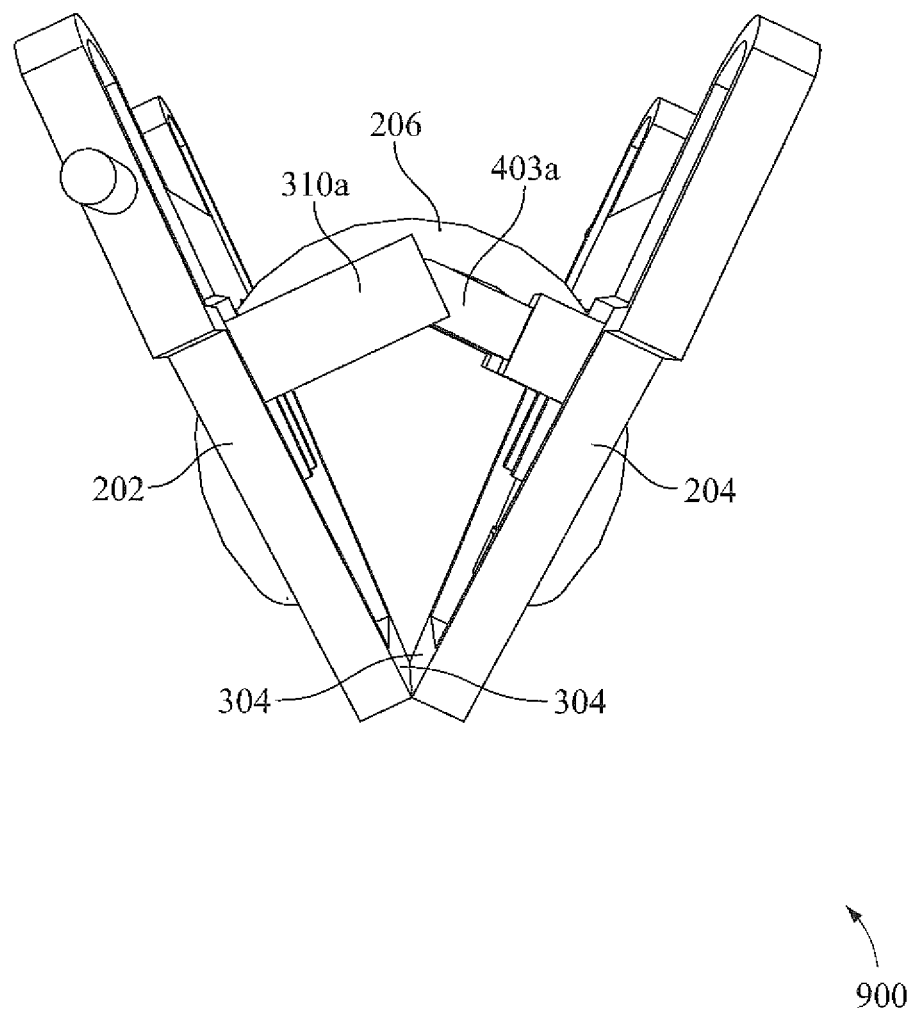
FIG. 9 is an end view of the major structural components of the RAIVES of FIG. 1A, according to an implementation.

FIG. 9 is an end view 900 of the major structural components of the RAIVES of FIG. 1A, according to an implementation. FIG. 9, in a manner similar to FIG. 7, illustrates the above-described inward spring bias of the connector spring 206 inwardly biasing the female-configured side plate 202 and the male-configured side plate 204 together to couple the female and male hinge elements (310a and 403a, respectively) configured as part of the female-configured side plate 202 and the male-configured side plate 204, respectively. The inward spring bias of the connector spring 206 biases the female-configured side plate 202 and the male-configured side plate 204 into a default closed configuration at the lower portions (for example, the gripping surfaces 304) of the female-configured side plate 202 and the male-configured side plate 204.

Figure 10:
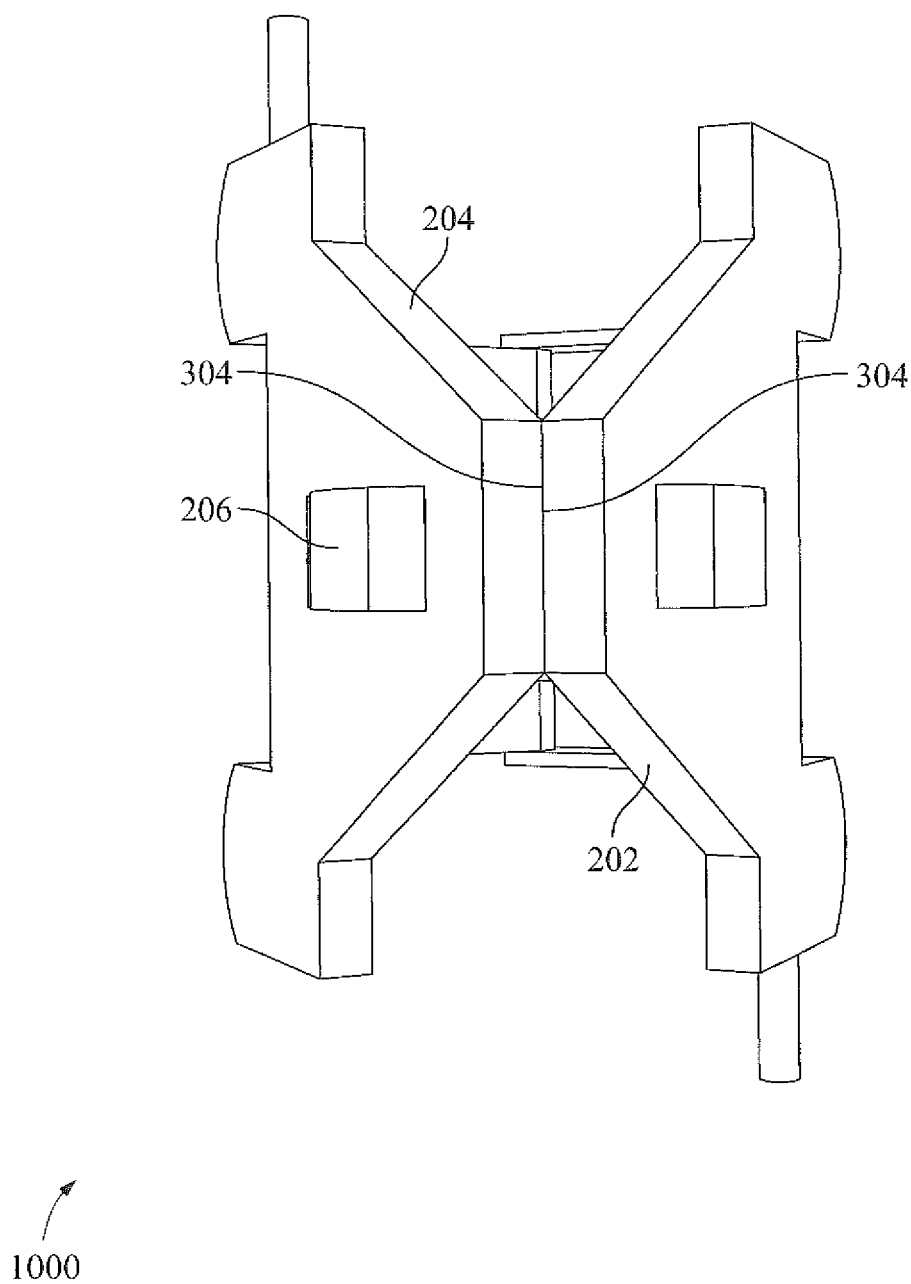
FIG. 10 is a closed bottom view of the major structural components of the RAIVES of FIG. 1A, according to an implementation.

FIG. 10 is a closed bottom view 1000 of the major structural components of the RAIVES of FIG. 1A, according to an implementation. FIG. 10 illustrates the inward spring bias of the connector spring 206 biasing the female-configured side plate 202 and the male-configured side plate 204 into a default closed configuration at the lower portions (for example, the gripping surfaces 304) of the female-configured side plate 202 and the male-configured side plate 204.

Figure 11:
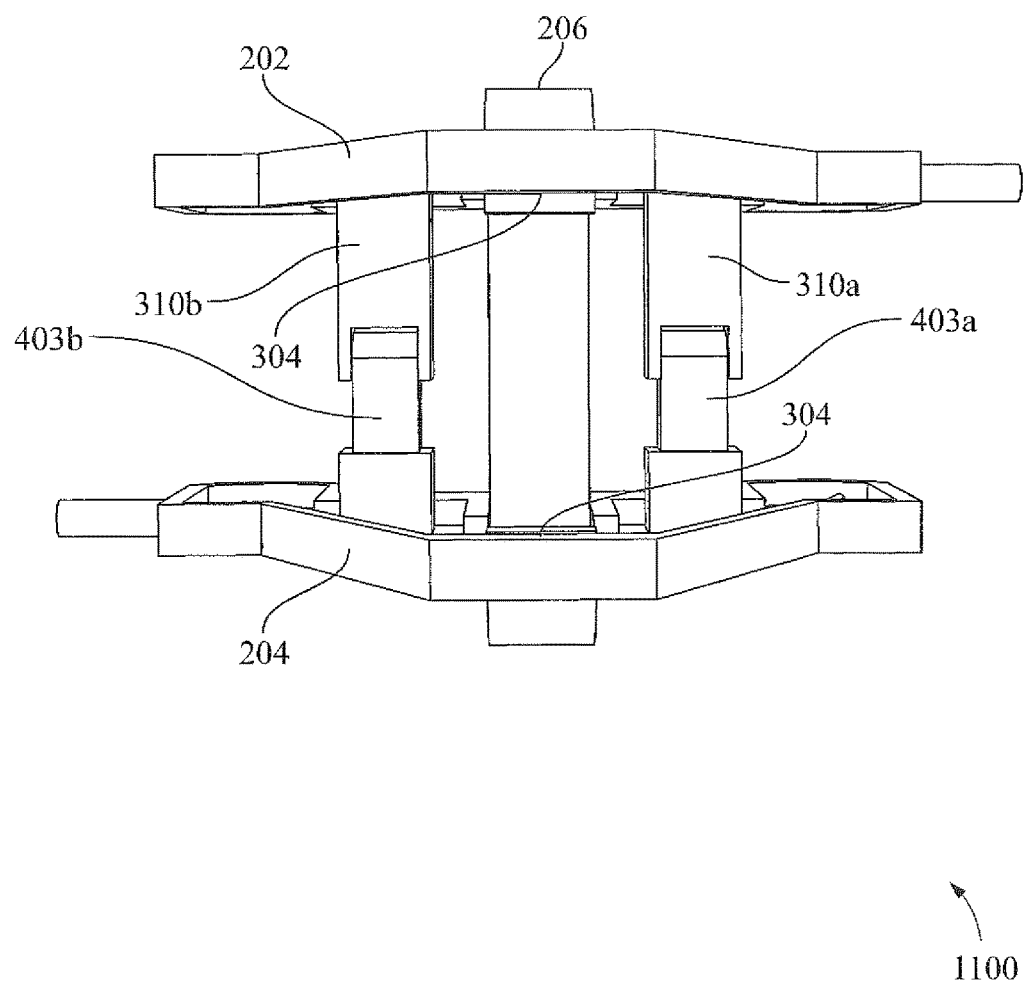
FIG. 11 is an open bottom view of the major structural components of the RAIVES of FIG. 1A, according to an implementation.

FIG. 11 is an open bottom view 1100 of the major structural components of the RAIVES of FIG. 1A, according to an implementation. FIG. 11 illustrates pressing the female-configured side plate 202 and the male-configured side plate 204 together (for example using pinch tabs—not illustrated) to produce force to overcome the inward spring bias of the connector spring 206. The applied force causes the female and male hinge elements (for example, 310a/310b and 403a/403b, respectively) configured as part of the female-configured side plate 202 and the male-configured side plate 204 to bear against each other and rotate to cause the lower portions of the female-configured side plate 202 and the male-configured side plate 204 (for example, the gripping surfaces 304) to open for engagement with a desired structure.

Figure 12A:
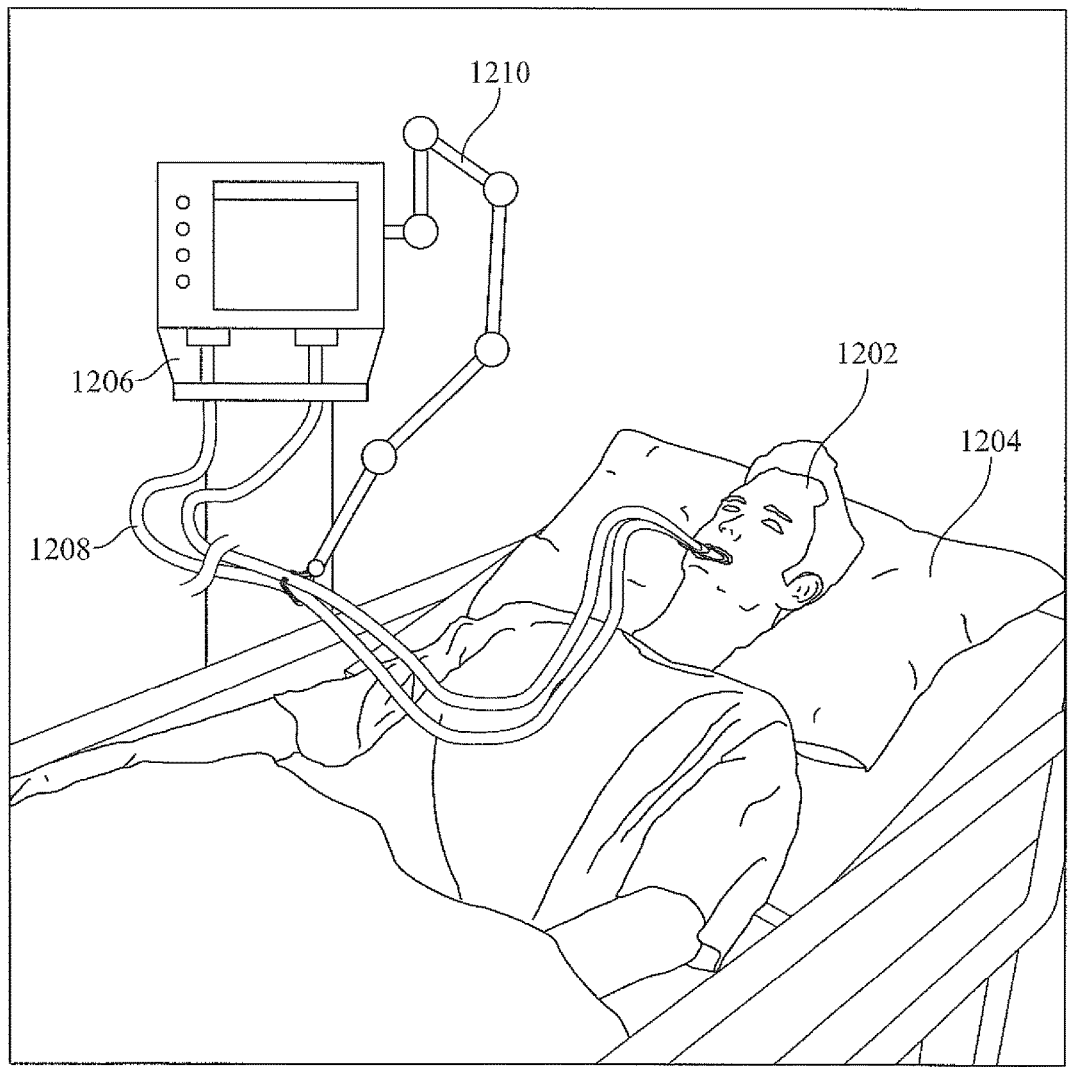
FIG. 12A is an illustration of a patient hooked up to a respiratory ventilation system in a conventional manner, according to an implementation.

FIG. 12A is an illustration 1200a of a patient attached to a respiratory ventilation system in a conventional manner, according to an implementation. In the illustration 1200a, a patient 1202 (in a supine position) on a patient treatment platform 1204 is attached to a mechanical ventilator 1206 using MED 1208 (here a respiratory airway tube). In typical implementations, a MED support 1210 (illustrated as separate free-standing support with a swinging arm) is used to support the MED 1208 between the patient 1202 and the mechanical ventilator 1206.

Figure 12B:
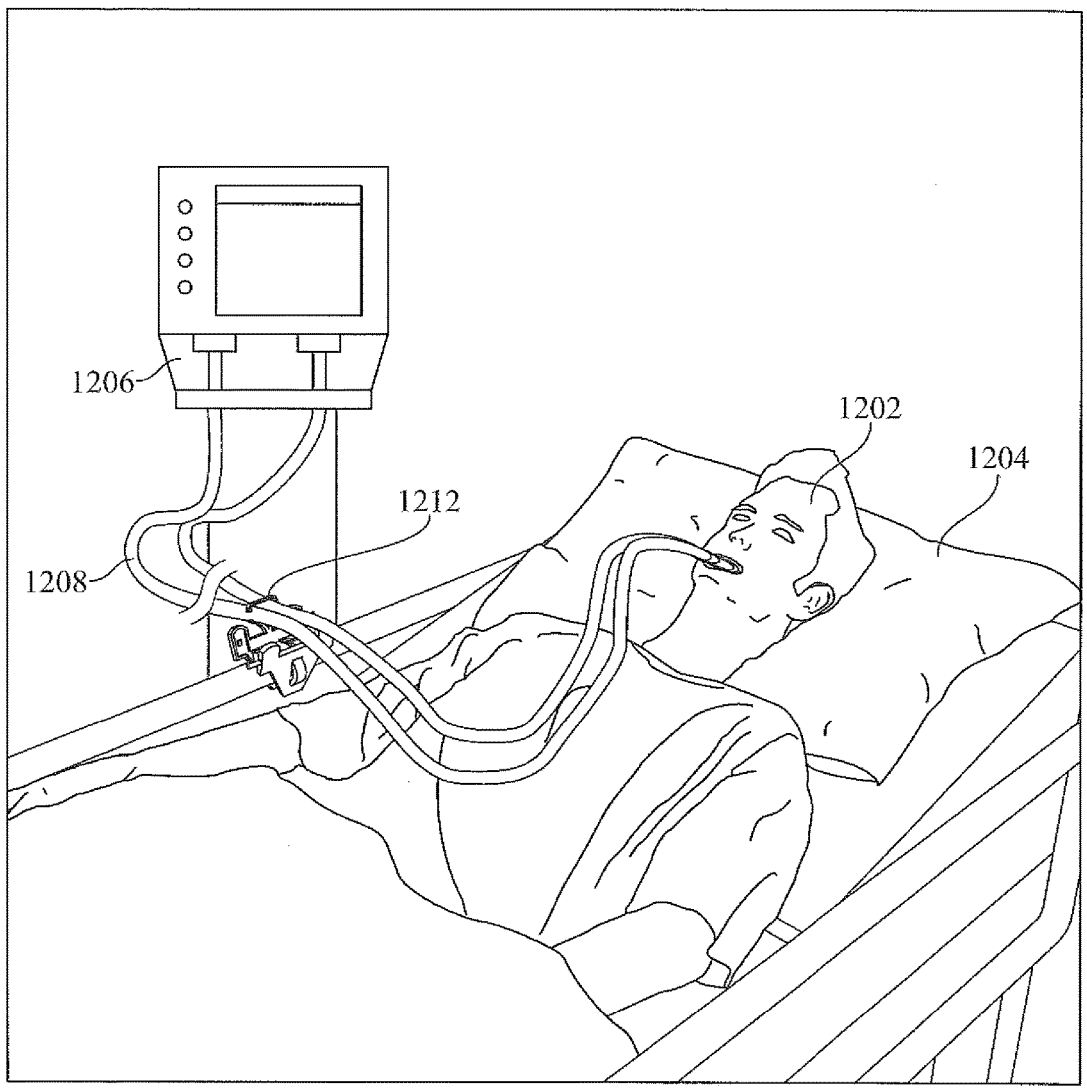
FIG. 12B is an illustration of a patient hooked up to the respiratory ventilation system using a respiratory-airway-configured RAIVES (refer to FIG. 13A), according to an implementation.

FIG. 12B is an illustration 1200b of a patient attached to the respiratory ventilation system using a respiratory-airway-configured RAIVES (refer to FIG. 13A), according to an implementation. In the illustration 1200b, the patient 1202 (in a supine position) on a patient treatment platform 1204 is attached to a mechanical ventilator 1206 using MED 1208 (here a respiratory airway tube) using a respiratory-airway-configured RAIVES 1212 attached to a rail of the patient treatment platform 1204. The use of the respiratory-airway-configured RAIVES 1212 permits easy placement of support for the MED 1208 and for easy adjustment of MED 1208 length between the mechanical ventilator 1206 and the patient 1202 (for example, if the patient is rotated into a lateral position).

Figure 13A:
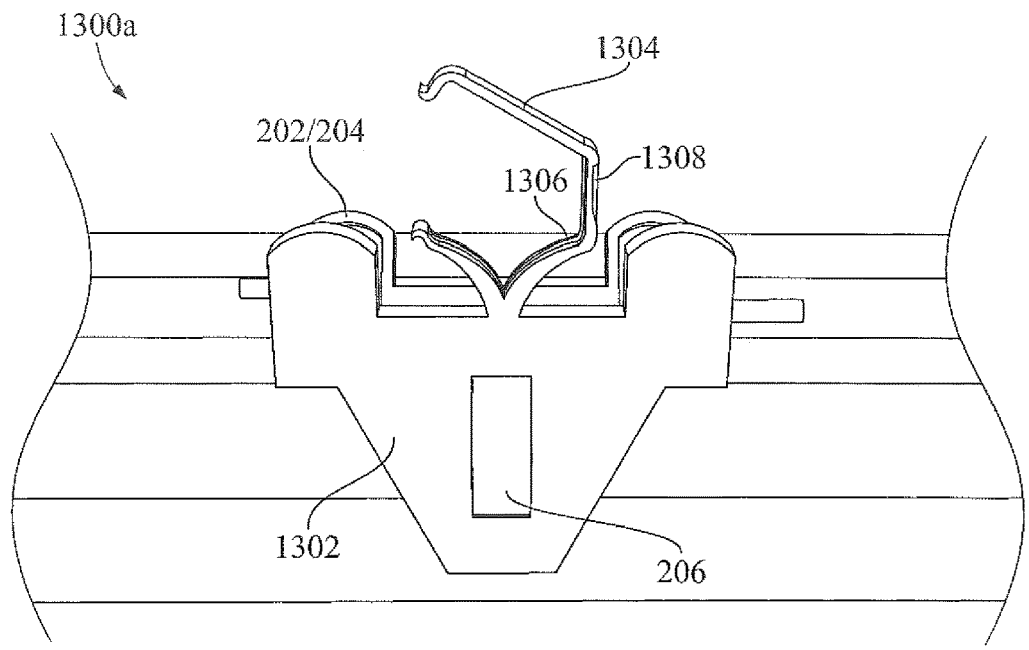
FIG. 13A is an exterior view of a respiratory-airway-configured RAIVES of FIG. 12B configured with a respiratory airway MED side plate, according to an implementation.

FIG. 13A is an exterior view 1300a of a respiratory-airway-configured RAIVES of FIG. 12B configured with a respiratory airway MED side plate, according to an implementation. The respiratory airway MED side plate 1302 is configured with an example respiratory MED hook 1304 (here, illustrated open) configured with respiratory MED hook detent 1306. In typical implementations, the interior configuration of respiratory airway MED side plate 1302 is similar to the interior configuration of either the female-configured side plate 202 or the male-configured side-plate 204 described above, depending upon whether the respiratory airway MED side plate 1302 is of a female or male configuration. In some implementations, the respiratory airway MED side plate 1302 (and side plate 202/204) can be configured to omit the locking pin 306, securing band attachment point 308, or the securing band 110a/110b. As will be appreciated by those of ordinary skill in the art, the example respiratory MED hook 1304 is a representative example to assist with understanding of the described concepts. Other configurations of the respiratory MED hook 1304 consistent with this disclosure are considered to be within the scope of this disclosure.

The inside diameter of the combination of the respiratory MED hook 1304 with respiratory MED hook detent 1306 is configured to engage with a respiratory airway MED "clipped"/pressed into the interior portion of the respiratory MED hook 1304. For example, the respiratory MED hook detent 1306 can be configured as a ridge, protrusion, extension, etc. configured as part of and extending from the interior of the MED hook 1304. In FIG. 13A, the MED hook detent 1306 is illustrated as a small ridge extending toward the interior of the MED hook 1304. The respiratory MED hook detent 1306 typically engages the outer surface of the respiratory airway tube at a particular position along the length of the respiratory airway MED (for example, a groove configured between lands in a land/groove configuration (for example, refer to FIG. 13B) or rests against the outer wall of a smooth-walled tube configuration (not illustrated)) to semi-secure the respiratory airway MED at the particular position with respect to the respiratory airway hook 1304.

In typical implementations, the respiratory MED hook 1304 is configured to permit opening and closing for easy insertion/removal of a respiratory airway MED. For example, the hinge 1308 of the respiratory MED hook 1304 can be configured with a detent-type assembly (not illustrated—for example, tabs or protrusions that are configured to engage with configured slots or divots, respectively, and leveraging the plasticity of the material the respiratory MED hook 1304 is configured of) to permit the hook to resist opening when in a closed position and to resist closing when in an open position without application of a moderate amount of force (for example, by a human hand). In other implementations, the hinge 1308 of the respiratory MED hook 1304 can be configured with a button release/spring-type assembly (not illustrated) to permit a button at or proximate to the hinge 1308 to be manipulated to automatically open the respiratory MED hook 1304. The respiratory MED hook 1304 can then be manually pushed closed (for example, with a human hand).

If a patient needs, for example, to be rotated from a supine to a lateral positon, a healthcare professional can grasp the respiratory airway MED and, prior to or while the patient is being rotated, pull the respiratory airway MED through the respiratory MED hook 1304 to a desired position along the respiratory airway MED (for example, by engaging successive grooves along the length of the respiratory airway MED or to a position along the smooth wall of a smooth-walled tube configuration). To reduce slack, the respiratory airway MED can be pulled back in the opposite direction to increase the length of the respiratory airway MED on the mechanical ventilator "side" of the respiratory-airway-configured RAIVES (for example, respiratory-airway-configured RAIVES 1212 of FIG. 12B) and to shorten the length of respiratory airway MED on the patient "side" of the respiratory-airway-configured RAIVES 1212.

In typical implementations, the respiratory MED hook detent 1306 is configured of an elastomeric material (for example, rubber, silicon, plastic, etc.) that has enough plasticity to engage with a respiratory airway MED, but to still allow the respiratory airway MED to slide within the respiratory MED hook 1304. The respiratory MED hook detent 1306 can be attached to the inner surface of the respiratory MED hook 1304 using, for example, adhesive, a track configured into the respiratory MED hook 1304 permitting the respiratory MED hook detent 1306 to be slid into place, etc.

In some implementations, the respiratory MED hook detent 1306 can be configured of a "sticky" elastomeric material. In these implementations, sliding the respiratory airway MED in either direction through the respiratory MED hook 1304 will cause the respiratory MED hook detent 1306 to stick to the respiratory airway MED causing a negative spring bias to return the respiratory airway MED to its original position. If it is desired to adjust the respiratory airway MED to a new position, a healthcare professional can grasp and remove the respiratory MED hook detent 1306 from the surface of the respiratory airway MED. The respiratory MED hook detent 1306 will spring back to the respiratory MED hook 1304 and re-adhere itself to a new position on the outer surface of the respiratory airway MED.

In typical implementations, a respiratory-airway-configured RAIVES is configured with a single respiratory airway MED side plate 1302. In other implementations, each side plate of a RAIVES can be configured with a respiratory airway MED side plate 1302. These implementations, permit more robust support of respiratory airway MEDs as the respiratory airway MEDs are pressed into two respiratory MED hooks 1304 per respiratory-airway-configured RAIVES.

In some implementations (not illustrated), the respiratory MED hook 1304 can be configured to rotate about its base, for example, three-hundred sixty degrees). These implementations permit respiratory airway MEDs to be guided in varying directions in relation to the mounted position of a respiratory-airway-configured RAIVES.

In some implementations, a separate respiratory MED hook 1304 can be configured (not illustrated) to attach to a conventional RAIVES side plate (for example, side plate 202/204 as described above) to form a respiratory airway MED side plate. For example, the base of the respiratory MED hook 1304 can be configured to slip over both sides of the side plate 202/204 at the attachment surface 316. The base of the respiratory MED hook 1304 can be adhered to the side plate 202/204 using adhesive, heat to fuse the material together, and the like.

In some implementations, one or more elements of the respiratory-airway-configured RAIVES (for example, the respiratory airway MED side plate 1302 or the connector spring 206) can be configured of a material (for example, plastics, metals, or ceramics) that can be disassembled, cleaned, sterilized in an autoclave or by chemical exposure (without sustaining damage due to high temperatures or chemical exposure, respectively), and reassembled for re-use.

Figure 13B:
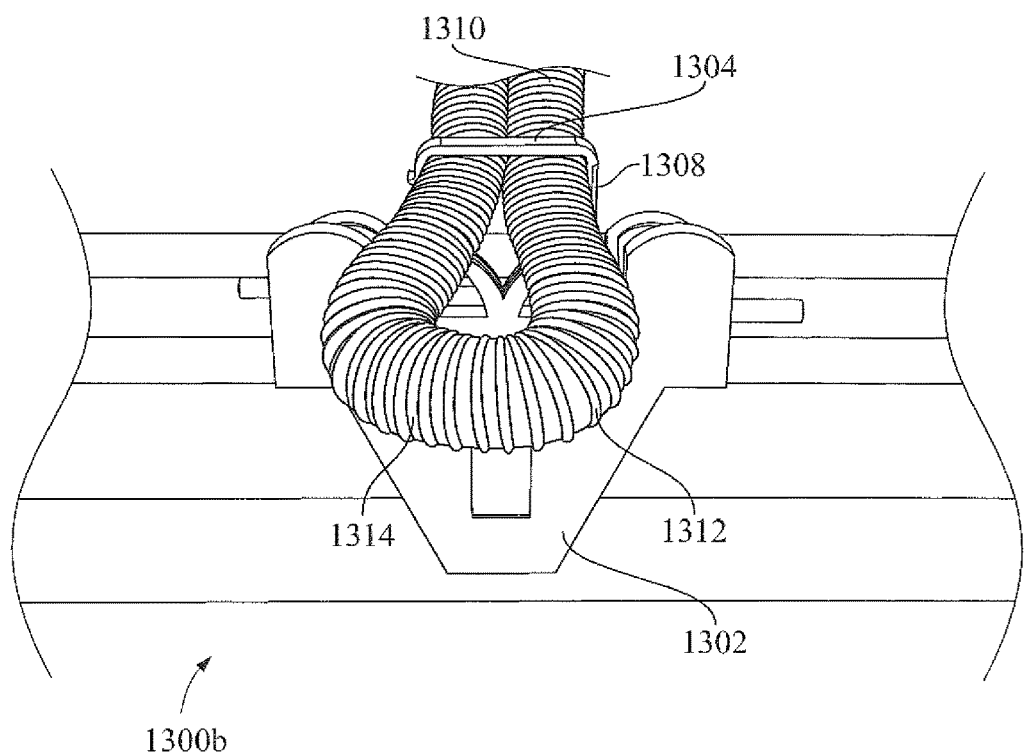
FIG. 13B is an exterior view of the respiratory-airway-configured RAIVES of FIG. 13A holding a respiratory airway MED, according to an implementation.

FIG. 13B is an exterior view 1300b of the respiratory-airway-configured RAIVES of FIG. 13A holding a respiratory airway MED, according to an implementation. The respiratory-airway-configured RAIVES is illustrated with a closed respiratory MED hook 1304 holding an example respiratory airway MED 1310 (here a respiratory airway tube).

Example respiratory MED 1310 is typically configured of highly-flexible, thermoplastic-type materials (for example, vinyl, DEHP-free PVC, polyethylene, or polypropylene). In the example illustration, respiratory airway MED 1310 is in a ridged- or land/groove-type tube configuration. Respiratory airway MED 1310 is configured with a series of perpendicular lands 1312 and grooves 1314 running substantially the entire length of the surface of the respiratory airway MED 1310. The configuration and flexibility of the respiratory airway MED 1310 permits the tube to bend, stretch, and compress at the grooves 1314. Other implementations (not illustrated) of respiratory airway MEDs can be configured with a smooth outer wall.

The following description provides an example use case of the RAIVES configuration illustrated in at least FIGS. 12A-12B, and 13A-13B. In some implementations, various described steps of the use case can be performed in a different order, consistent with this disclosure. Opening and engagement of the RAIVES with a structure (for example, a hospital bed rail) is analogous to the description above with respect to the RAIVES configuration described in at least FIGS. 1A, 1B, and 2. Once secured to a desired structure, a respiratory airway MED attached on one end to a mechanical ventilator (including associated humidification and other ventilation equipment) and to a patient on the other end can be "clipped"/pressed into the interior portion of the respiratory MED hook against configured respiratory MED hook detent. The respiratory MED hook detent engage the outer surface at a particular position along the length of the respiratory airway MED (for example, a groove between lands in a land/groove configuration of FIG. 13B or rest against the outer wall of a smooth-walled tube configuration (not illustrated)) to semi-secure the respiratory airway MED at the particular position with respect to the respiratory MED hook. If a patient needs, for example, to be rotated from a supine to a lateral positon, a healthcare professional can grasp the respiratory airway MED and, prior to or while the patient is being rotated, pull the respiratory airway MED through the respiratory MED hook to a desired position along the respiratory airway MED is reached (for example, engaging successive grooves along the length of the respiratory airway MED or to a position along the smooth wall of a smooth-walled tube configuration). To reduce slack, the respiratory airway MED can be pulled back in the opposite direction to increase the length of the respiratory airway MED on the mechanical ventilator "side" of the RAIVES and to shorten the length of respiratory airway MED on the patient "side" of the RAIVES.

In some implementations, the described RAIVES configurations can include one or more sensors and computers (not illustrated). For example, a miniaturized computer system (for example, computer 1402 below) can be attached to one of the female-configured side plate 202 or male-configured side plate 202. The computer can include, among other things, various sensors (for example, auditory, infrared, magnetic, temperature, pressure, orientation, flow, etc.), a battery, a timer, light-emitting elements (for example, LEDs, bulbs, etc.), audio emitting elements, WIFI/wired networking capability, and the like. As an example of use, a computer-equipped RAIVES could signal a specific orientation angle or position on a hospital bed rail, monitor that fluids are flowing through a particular IV tube, monitor that electricity is flowing through a heart monitoring lead wire, etc. The computer-equipped RAIVES could be networked into a hospital computer/monitoring system (including other computer-equipped RAIVES) to provide additional medical information to healthcare providers. Alarms (for example, visual, auditory, network messages, etc.) could be generated to alert healthcare professionals if pre-programmed thresholds are met or exceeded. In some implementations, the above-described guide plate 208 of FIGS. 2 and 6A can be configured with one or more of the above-described sensors to provide monitoring of one or more MEDS in proximity to the guide plate 208. In some implementations, particular sensors can be attached to particular MEDS for individual monitoring purposes (for example, a sensor lead from the computer system can be attached to a respiratory tube to provide auditory monitoring of air flow through the respiratory tube). Other examples will be apparent to those of ordinary skill in the art.

Figure 14:
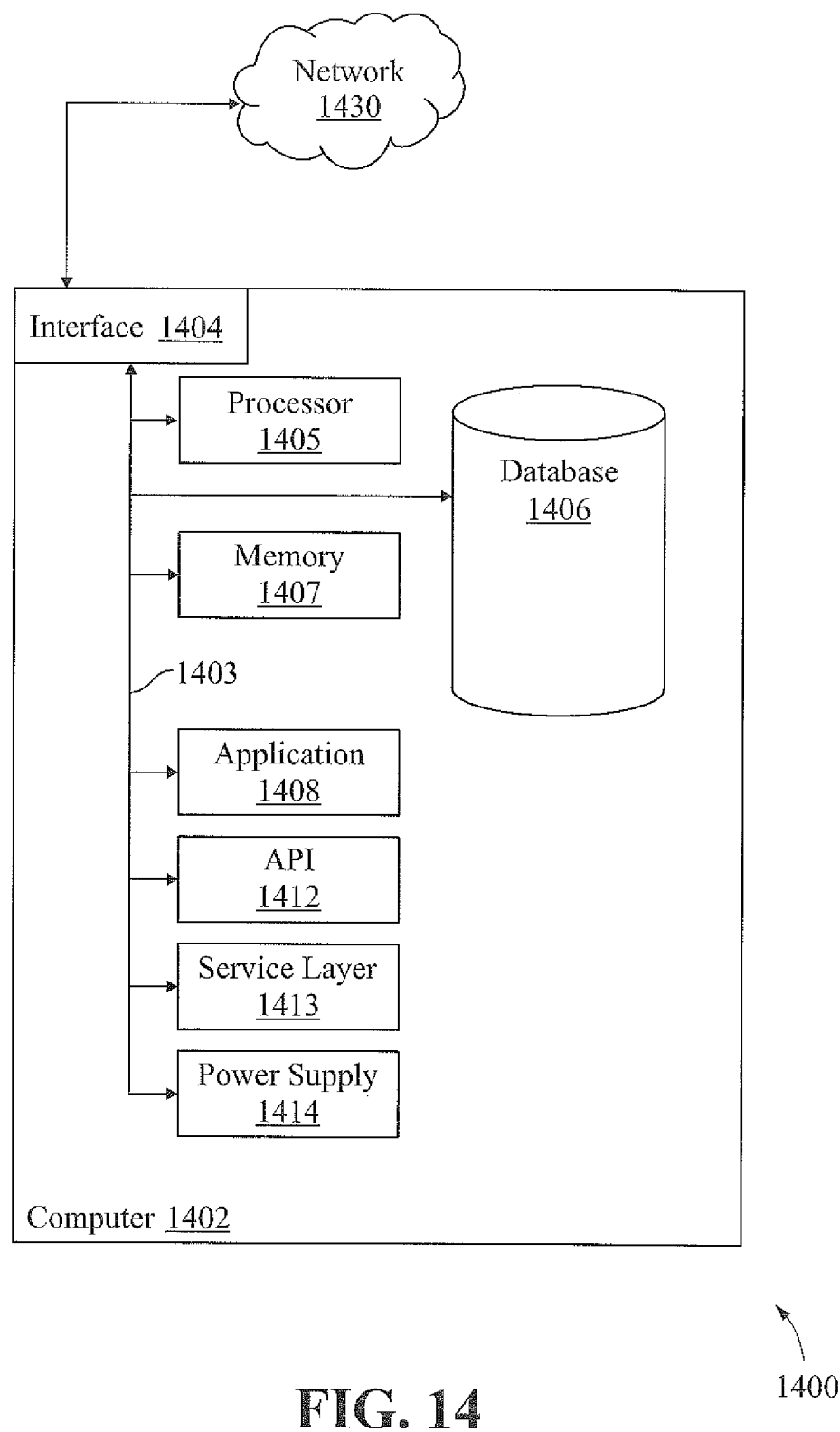
FIG. 14 is a block diagram of an exemplary computer system used to provide computational functionalities associated with described algorithms, methods, functions, processes, flows, and procedures as described in the instant disclosure, according to an implementation.

FIG. 14 is a block diagram of an example computer system 1400 used to provide computational functionalities associated with described algorithms, methods, functions, processes, flows, and procedures as described in the instant disclosure, according to an implementation. The illustrated computer 1402 is intended to encompass any computing device such as a server, desktop computer, laptop/notebook computer, wireless data port, smart phone, personal data assistant (PDA), tablet computing device, one or more processors within these devices, or any other suitable processing device, including physical or virtual instances (or both) of the computing device. Additionally, the computer 1402 may comprise a computer that includes an input device, such as a keypad, keyboard, touch screen, or other device that can accept user information, and an output device that conveys information associated with the operation of the computer 1402, including digital data, visual, or audio information (or a combination of information), or a GUI.

The computer 1402 can serve in a role as a client, network component, a server, a database or other persistency, or any other component (or a combination of roles) of a computer system for performing the subject matter described in the instant disclosure. The illustrated computer 1402 is communicably coupled with a network 1430. In some implementations, one or more components of the computer 1402 may be configured to operate within environments, including cloud-computing-based, local, global, or other environment (or a combination of environments).

At a high level, the computer 1402 is an electronic computing device operable to receive, transmit, process, store, or manage data and information associated with the described subject matter. According to some implementations, the computer 1402 may also include or be communicably coupled with an application server, e-mail server, web server, caching server, streaming data server, or other server (or a combination of servers).

The computer 1402 can receive requests over network 1430 from a client application (for example, executing on another computer 1402) and responding to the received requests by processing the received requests using an appropriate software application(s). In addition, requests may also be sent to the computer 1402 from internal users (for example, from a command console or by other appropriate access method), external or third-parties, other automated applications, as well as any other appropriate entities, individuals, systems, or computers.

Each of the components of the computer 1402 can communicate using a system bus 1403. In some implementations, any or all of the components of the computer 1402, both hardware or software (or a combination of hardware and software), may interface with each other or the interface 1404 (or a combination of both) over the system bus 1403 using an application programming interface (API) 1412 or a service layer 1413 (or a combination of the API 1412 and service layer 1413). The API 1412 may include specifications for routines, data structures, and object classes. The API 1412 may be either computer-language independent or dependent and refer to a complete interface, a single function, or even a set of APIs. The service layer 1413 provides software services to the computer 1402 or other components (whether or not illustrated) that are communicably coupled to the computer 1402. The functionality of the computer 1402 may be accessible for all service consumers using this service layer. Software services, such as those provided by the service layer 1413, provide reusable, defined functionalities through a defined interface. For example, the interface may be software written in JAVA, C++, or other suitable language providing data in extensible markup language (XML) format or other suitable format. While illustrated as an integrated component of the computer 1402, alternative implementations may illustrate the API 1412 or the service layer 1413 as stand-alone components in relation to other components of the computer 1402 or other components (whether or not illustrated) that are communicably coupled to the computer 1402. Moreover, any or all parts of the API 1412 or the service layer 1413 may be implemented as child or sub-modules of another software module, enterprise application, or hardware module without departing from the scope of this disclosure.

The computer 1402 includes an interface 1404. Although illustrated as a single interface 1404 in FIG. 14, two or more interfaces 1404 may be used according to particular needs, desires, or particular implementations of the computer 1402. The interface 1404 is used by the computer 1402 for communicating with other systems that are connected to the network 1430 (whether illustrated or not) in a distributed environment. Generally, the interface 1404 comprises logic encoded in software or hardware (or a combination of software and hardware) and is operable to communicate with the network 1430. More specifically, the interface 1404 may comprise software supporting one or more communication protocols associated with communications such that the network 1430 or interface's hardware is operable to communicate physical signals within and outside of the illustrated computer 1402.

The computer 1402 includes a processor 1405. Although illustrated as a single processor 1405 in FIG. 14, two or more processors may be used according to particular needs, desires, or particular implementations of the computer 1402. Generally, the processor 1405 executes instructions and manipulates data to perform the operations of the computer 1402 and any algorithms, methods, functions, processes, flows, and procedures as described in the instant disclosure.

The computer 1402 also includes a database 1406 that can hold data for the computer 1402 or other components (or a combination of both) that can be connected to the network 1430 (whether illustrated or not). For example, database 1406 can be an in-memory, conventional, or other type of database storing data consistent with this disclosure. In some implementations, database 1406 can be a combination of two or more different database types (for example, a hybrid in-memory and conventional database) according to particular needs, desires, or particular implementations of the computer 1402 and the described functionality. Although illustrated as a single database 1406 in FIG. 14, two or more databases (of the same or combination of types) can be used according to particular needs, desires, or particular implementations of the computer 1402 and the described functionality. While database 1406 is illustrated as an integral component of the computer 1402, in alternative implementations, database 1406 can be external to the computer 1402.

The computer 1402 also includes a memory 1407 that can hold data for the computer 1402 or other components (or a combination of both) that can be connected to the network 1430 (whether illustrated or not). For example, memory 1407 can be random access memory (RAM), read-only memory (ROM), optical, magnetic, and the like storing data consistent with this disclosure. In some implementations, memory 1407 can be a combination of two or more different types of memory (for example, a combination of RAM and magnetic storage) according to particular needs, desires, or particular implementations of the computer 1402 and the described functionality. Although illustrated as a single memory 1407 in FIG. 14, two or more memories 1407 (of the same or combination of types) can be used according to particular needs, desires, or particular implementations of the computer 1402 and the described functionality. While memory 1407 is illustrated as an integral component of the computer 1402, in alternative implementations, memory 1407 can be external to the computer 1402.

The application 1408 is an algorithmic software engine providing functionality according to particular needs, desires, or particular implementations of the computer 1402, particularly with respect to functionality described in this disclosure. For example, application 1408 can serve as one or more components, modules, applications, etc. Further, although illustrated as a single application 1408, the application 1408 may be implemented as multiple applications 1408 on the computer 1402. In addition, although illustrated as integral to the computer 1402, in alternative implementations, the application 1408 can be external to the computer 1402.

The computer 1402 also includes a power supply 1414. The power supply 1414 can include a rechargeable or non-rechargeable battery than can be configured to be either user- or non-user-replaceable. In some implementations, the power supply 1414 can include power-conversion or management circuits (including recharging, standby, or other power management functionality). In some implementations, the power-supply 1414 can include a power plug to allow the computer 1402 to be plugged into a wall socket or other power source to power the computer 1402, recharge a rechargeable battery, etc.

There may be any number of computers 1402 associated with, or external to, a computer system containing computer 1402, each computer 1402 communicating over network 1430. Further, the term "client," "user," and other appropriate terminology may be used interchangeably as appropriate without departing from the scope of this disclosure. Moreover, this disclosure contemplates that many users may use one computer 1402, or that one user may use multiple computers 1402.

Described implementations of the subject matter can include one or more features, alone or in combination.

For example, in a first implementation, an apparatus, comprising: a female-configured side plate and a male-configured side plate; a connector spring configured to engage with and to couple together the female-configured side plate and the male-configured side plate, the connector spring providing an inward spring bias to bias a lower portion of the female-configured side plate and a lower portion of the male-configured side plate together into a default closed position; raised guidance elements; and a plurality of securing bands.

The foregoing and other described implementations can each optionally include one or more of the following features:

A first feature, combinable with any of the following features, wherein the female-configured side plate and the male-configured side plate are each configured to define a connector spring engagement slot and a connector spring locking slot.

A second feature, combinable with any of the previous or following features, wherein the connector spring comprises two angled locking ends, each angled locking end configured to engage with the connector spring locking slot defined by the female-configured side plate and the male-configured side plate.

A third feature, combinable with any of the previous or following features, wherein an upper portion of the female-configured side plate and the male-configured side plate are each configured with a plurality of pinch tabs to permit the lower portion of the female-configured side plate and the lower portion of the male-configured side plate to be separated when the pinch tabs are manipulated toward each other to overcome the inward spring bias of the connector spring.

A fourth feature, combinable with any of the previous or following features, wherein the raised guidance elements are configured to secure a medical extension device between the plurality of pinch tabs.

A fifth feature, combinable with any of the previous or following features, wherein each of the plurality of securing bands is attached to a side of the female-configured side plate or the male-configured side plate and stretched to engage with a locking pin configured proximate to a pinch tab of the plurality of pinch tabs on each of the female-configured side plate and the male-configured side plate.

A sixth feature, combinable with any of the previous or following features, wherein each securing band of the plurality of securing bands is configured with a stationary end and an engagement ring; wherein the stationary end is used to attach the securing band to the side of the female-configured side plate or the male-configured side plate and the engagement ring is used to engage the securing band with a particular locking pin.

A seventh feature, combinable with any of the previous or following features, wherein the raised guidance elements are configured as part of a guidance plate attached to the upper surface of the female-configured side plate and the male-configured side plate.

In a second implementation, an apparatus, comprising: a female-configured side plate and a male-configured side plate, wherein the female-configured side plate comprises a plurality of female hinge elements with corresponding engagement pockets configured to engage with engagement portions of corresponding male hinge elements configured as part of the male-configured side plate; a connector spring configured to engage with and to couple together the female-configured side plate and the male-configured side plate; raised guidance elements; and a plurality of securing bands configured to secure a medical extension device to the raised guidance elements.

The foregoing and other described implementations can each optionally include one or more of the following features:

A first feature, combinable with any of the following features, wherein an engagement portion of a particular male hinge element or an engagement pocket of a particular female hinge element is configured with an elastomeric-type buffer material to cushion engagement between the particular female hinge element and the particular male hinge element.

A second feature, combinable with any of the previous or following features, wherein the female-configured side plate and the male-configured side plate are each configured to define a connector spring engagement slot and a connector spring locking slot.

A third feature, combinable with any of the previous or following features, wherein the connector spring comprises two angled locking ends, each angled locking end configured to engage with the connector spring locking slot defined by the female-configured side plate and the male-configured side plate.

A fourth feature, combinable with any of the previous or following features, wherein the connector spring is configured to provide an inward spring bias to bias a lower portion of the female-configured side plate and the lower portion of the male-configured side plate together into a default closed position.

A fifth feature, combinable with any of the previous or following features, wherein an upper portion of the female-configured side plate and an upper portion of the male-configured side plate are each configured with a plurality of pinch tabs to permit the lower portion of the female-configured side plate and the lower portion of the male-configured side plate to be separated when the pinch tabs are manipulated toward each other to overcome the inward spring bias of the connector spring.

A sixth feature, combinable with any of the previous or following features, wherein each securing band of the plurality of securing bands is configured with a stationary end and an engagement ring; wherein the stationary end is used to attach the securing band to the side of the female-configured side plate or the male-configured side plate and the engagement ring is used to engage the securing band with a particular locking pin.

A seventh feature, combinable with any of the previous or following features, wherein the raised guidance elements are configured as part of a guidance plate attached to the upper portion of the female-configured side plate and the upper portion of the male-configured side plate.

In a third implementation, a method, comprising: manipulating a plurality of pinch tabs together, wherein the plurality of pinch tabs are configured as part of each of an upper portion of a female-configured side plate and an upper portion of a male-configured side plate; and wherein the manipulation overcomes an inward spring bias of a connector spring biasing a lower portion of the female-configured side plate and a lower portion of the male-configured side plate together into a default closed position; separating the lower portion of the female-configured side plate and the lower portion of the male-configured side plate; and allowing the manipulated pinch tabs to separate to grip a patient treatment platform with the lower portion of the female-configured side plate and the lower portion of the male-configured side plate.

The foregoing and other described implementations can each optionally include one or more of the following features:

A first feature, combinable with any of the following features, comprising receiving a medical extension device between the plurality of pinch tabs corresponding to either the female-configured side plate or the male-configured side plate.

A second feature, combinable with any of the previous or following features, comprising securing, using a securing band, the received medical extension device against raised guidance elements attached to the upper portion of the female-configured side plate or the upper portion of the male-configured side plate.

A third feature, combinable with any of the previous or following features, comprising: manipulating the plurality of pinch tabs together to overcome the inward spring bias of the connector spring; separating the lower portion of the female-configured side plate and the lower portion of the male-configured side plate; and allowing the manipulated pinch tabs to separate to grip the patient treatment platform at a different position with the lower portion of the female-configured side plate and the lower portion of the male-configured side plate.

Some implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, that is, one or more modules of computer program instructions encoded on a tangible, non-transitory, computer-readable computer-storage medium for execution by, or to control the operation of, data processing apparatus. Alternatively or in addition, the program instructions can be encoded on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data may be less than 1 ms, less than 1 sec., less than 5 secs., etc. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) may be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, IOS, or any other suitable conventional operating system.

A computer program, which may also be referred to or described as a program, software, a software application, a module, a software module, a script, or code can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The methods, processes, logic flows, etc. described in this specification can be performed by one or more programmable computers executing one or more computer programs to perform functions by operating on input data and generating output. The methods, processes, logic flows, etc. can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM), or both. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD+/−R, DVD-RAM, and DVD-ROM disks. The memory may store various objects or data, including caches, classes, frameworks, applications, backup data, jobs, web pages, web page templates, database tables, repositories storing dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with this disclosure), all or a portion of the Internet, or any other communication system or systems at one or more locations (or a combination of communication networks). The network may communicate with, for example, Internet Protocol (IP) packets, Frame Relay frames, Asynchronous Transfer Mode (ATM) cells, voice, video, data, or other suitable information (or a combination of communication types) between network addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although features may be described above as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the implementations described above should not be understood as requiring such separation or integration in all implementations, and it should be understood that the described program components and systems can generally be integrated together in a single software product or packaged into multiple software products.

Accordingly, the above description of example implementations does not define or constrain this disclosure. Other changes, substitutions, and alterations are also possible without departing from the spirit and scope of this disclosure.

Furthermore, one or more of the claimed implementations below are considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. An apparatus, comprising:
  a female-configured side plate and a male-configured side plate;
  a connector spring configured to engage with and to couple together the female-configured side plate and the male-configured side plate, the connector spring providing an inward spring bias to bias a lower portion of the female-configured side plate and a lower portion of the male-configured side plate together into a default closed position, wherein an upper portion of the female-configured side plate and the male-configured side plate are each configured with a plurality of pinch tabs to permit the lower portion of the female-configured side plate and the lower portion of the male-configured side plate to be separated when the pinch tabs are manipulated toward each other to overcome the inward spring bias of the connector spring;
  raised guidance elements, wherein the raised guidance elements are configured to secure a medical extension device between either or both of the plurality of pinch tabs; and
  a plurality of securing bands, wherein each of the plurality of securing bands is attached to a side of the female-configured side plate or a side of the male-configured side plate and stretched to engage with a locking pin configured proximate to a pinch tab of the plurality of pinch tabs on each of the female-configured side plate and the male-configured side plate.

2. The apparatus of claim 1, wherein the female-configured side plate and the male-configured side plate are each configured to define a connector spring engagement slot and a connector spring locking slot.

3. The apparatus of claim 2, wherein the connector spring comprises two angled locking ends, each angled locking end configured to engage with the connector spring locking slot defined by the female-configured side plate and the male-configured side plate.

4. The apparatus of claim 1, wherein each securing band of the plurality of securing bands is configured with a stationary end and an engagement ring; wherein the stationary end is used to attach the securing band to the side of the female-configured side plate or the side of the male-configured side plate and the engagement ring is used to engage the securing band with the locking pin that is also located on the female-configured side plate or the male-configured side plate.

5. The apparatus of claim 1, wherein the raised guidance elements are configured as part of a guidance plate attached to an upper surface of the female-configured side plate and to an upper surface of the male-configured side plate.

6. An apparatus, comprising:
a female-configured side plate and a male-configured side plate, wherein the female-configured side plate comprises a plurality of female hinge elements with corresponding engagement pockets configured to engage with engagement portions of corresponding male hinge elements configured as part of the male-configured side plate;
a connector spring configured to engage with and to couple together the female-configured side plate and the male-configured side plate, wherein the female-configured side plate and the male-configured side plate are each configured to define a connector spring engagement slot and a connector spring locking slot;
raised guidance elements; and
a plurality of securing bands configured to secure a medical extension device to the raised guidance elements.

7. The apparatus of claim 6, wherein an engagement portion of each of the male hinge elements of the plurality of male hinge elements or an engagement pocket of each of the female hinge elements of the plurality of female hinge elements is configured with an elastomeric-type buffer material to cushion engagement between the female hinge elements and the male hinge elements.

8. The apparatus of claim 6, wherein the connector spring comprises two angled locking ends, each angled locking end configured to engage with the connector spring locking slot defined by the female-configured side plate and the male-configured side plate.

9. The apparatus of claim 6, wherein the connector spring is configured to provide an inward spring bias to bias a lower portion of the female-configured side plate and a lower portion of the male-configured side plate together into a default closed position.

10. The apparatus of claim 9, wherein an upper portion of the female-configured side plate and an upper portion of the male-configured side plate are each configured with a plurality of pinch tabs to permit the lower portion of the female-configured side plate and the lower portion of the male-configured side plate to be separated when the pinch tabs are manipulated toward each other to overcome the inward spring bias of the connector spring.

11. The apparatus of claim 6, wherein each securing band of the plurality of securing bands is configured with a stationary end and an engagement ring;
wherein the stationary end is used to attach the securing band to a side of the female-configured side plate or to a side of the male-configured side plate, and wherein the engagement ring is used to engage the securing band with a locking pin.

12. The apparatus of claim 6, wherein the raised guidance elements are configured as part of a guidance plate attached to an upper portion of the female-configured side plate and an upper portion of the male-configured side plate.

* * * * *